United States Patent [19]

Cercek et al.

[11] Patent Number: 5,580,561

[45] Date of Patent: Dec. 3, 1996

[54] METHODS AND PHARMACEUTICAL COMPOSITIONS FOR BLOCKING SUPPRESSION OF IMMUNE DEFENSE MECHANISMS USING AN ANTIBODY, A FACTOR, OR AN ANTISENSE PEPTIDE

[76] Inventors: Boris Cercek; Lea Cercek, both of 4318 Camphor Ave., Yorba Linda, Calif. 92686

[21] Appl. No.: 2,466

[22] Filed: Jan. 8, 1993

Related U.S. Application Data

[63] Continuation-in-part of Ser. No. 539,686, Jun. 18, 1990, Pat. No. 5,270,171, which is a continuation-in-part of Ser. No. 167,007, Mar. 3, 1988, abandoned, which is a continuation-in-part of Ser. No. 22,759, Mar. 6, 1987, abandoned.

[51] Int. Cl.$^6$ .......................... C07K 16/24; A61K 39/00
[52] U.S. Cl. .................... 424/145.1; 424/139.1; 424/185.1; 530/387.9; 530/388.1; 530/388.2; 530/388.7; 530/388.25; 530/388.8; 530/324; 530/325; 530/351; 514/12; 514/21
[58] Field of Search ...................... 530/325, 326, 530/327, 328, 387.1, 387.9, 388.1, 388.2, 388.7, 388.25, 388.8, 324, 351, 403; 424/85.1, 85.2, 85.4, 85.8, 130.1, 139.1, 145.1, 85.1; 514/12, 13, 14, 15, 16, 2, 21

[56] References Cited

U.S. PATENT DOCUMENTS

| | | | |
|---|---|---|---|
| 4,391,904 | 7/1983 | Litman et al. | 435/7.9 |
| 4,444,744 | 4/1984 | Goldenberg et al. | |
| 4,645,738 | 2/1987 | Knowles et al. | |
| 5,270,171 | 12/1993 | Cercek et al. | 435/29 |

FOREIGN PATENT DOCUMENTS

| | | |
|---|---|---|
| 0328403 | 8/1989 | European Pat. Off. |
| 0369816A2 | 5/1990 | European Pat. Off. |
| WO8707382 | 12/1987 | WIPO |
| 8806595 | 9/1988 | WIPO |
| WO8806595 | 9/1988 | WIPO |
| WO89/07445 | 8/1989 | WIPO |
| WO8908118 | 9/1989 | WIPO |
| WO8908662 | 9/1989 | WIPO |
| WO9004785 | 5/1990 | WIPO |
| WO9119736 | 12/1991 | WIPO |

OTHER PUBLICATIONS

McCabe et al (1988) Cancer Res 48:4348–4353.
Rawlins et al (1976) Bri. J. Cancer 34:613–618.
Kashima et al (1985) Nature 313:402–404.
Beutler et al (1986) Nature 320:584–588.
Alberts et al (1983) "The Moleculer Biology of the Cell", Garland Publishing, Inc., New York, p. 213.
Harne et al (1993) Trends in Biotech 11:42–44.
Gregouadis et al (1993) Trends in Biotech. 11:440–442.
American Type Culture Collection Catalogue of Cell Lines and Hyperdomes, 7th edition (1992) R. Hay et al, eds., pp. 129–130.
Chenuios Catalog (1986), pp. 6 and 23.
Intelliginetics Software Sequence Search Comparison, Conducted Nov. 9, 1994. Seq. 1D No. 1 (p. 8), Sq. 1D No. 2 (p. 10), Sq 1D No. 6 (p. 8). Cote et al (1983) Proc. Nat'l. Acad. Sci. 80:2026–2030.
Albein et al (eds.) (1972) "Basic Neuochemistry," Little, Brown, and Company, Boston, pp. 503–509.
Rosenberg et al (1984) Nature 312:77–80.
Cercek et al (1993) Cancer Detect. Prev. 17(3):433–445.
Carrell et al (1982) Nature 298:329–334.
Joding (1983) "Monoclonal Antibodies", Academic Press, Orlando, pp. 56–91, 250–259 & 29.
Chaitchik et al (1985) Eur. J. Cancer Clin. Oncol. 21(10):1165–1170.
Jaffe (1985) in "Kirk–Othmer Concise Encyclopedia of Chemical Technology", John Wiley & Sons, New York, pp. 1236–1238.
Geuzyme Catalogy (1993), pp. 210–211.
L. Cercek, et al., "Biophysical Differentiation Between Lymphocytes from Healthy Donors, Patients with Malignant Diseases and Other Disorders," *Brit. J. Cancer* 29:345–352 (1974).
L. Cercek & B. Cercek, "Application of the Phenomenon of Changes in the Structuredness of Cytoplasmic Matrix (SCM) in the Diagnosis of Malignant Disorders: A Review," *Europ. J. Cancer* 13:903–915 (1977).
L. Cercek & B. Cercek, "Changes in SCM–Responses of Lymphocytes in Mice After Implantation with Ehrlich Ascites Cells," *Europ. J. Cancer* 17:167–171 (1981).
L. Cercek & B. Cercek, "Changes in the SCM Response Ratio ($RR_{SCM}$) After Surgical Removal of Malignant Tissue," *Brit. J. Cancer* 31:250–251.
L. Cercek & B. Cercek, "Apparent Tumour Specificity with the SCM Test," *Brit J. Cancer* 31:252–253 (1975).
S. Chaitchik et al., "Tumor Specificity of the SCM Test for Cancer Diagnosis," *Eur. J. Cancer Clin. Oncol.* 21:1165–1170 (1985).

(List continued on next page.)

*Primary Examiner*—Toni R. Scheiner
*Attorney, Agent, or Firm*—Merchant, Gould, Smith, Edell, Welter & Schmidt

[57] ABSTRACT

A method for blocking suppression of at least one of the natural killer (NK) and lymphocyte activated killer (LAK) cytotoxicity mechanisms in lymphocytes of cancer patients comprises administering to a cancer patient an agent capable of blocking the cytotoxicity suppressive activities of a peptide capable of inducing a detectable decrease in the structuredness of the cytoplasmic matrix in lymphocytes isolated from a patient with cancer (an SCM-factor peptide) in a quantity sufficient to block suppression of at least one of the natural killer (NK) and lymphocyte activated killer (LAK) cytotoxicity mechanisms. The agent can comprise an antibody or an antisense peptide. The invention also includes pharmaceutical compositions and kits for blocking suppression of cytotoxicity.

30 Claims, 2 Drawing Sheets

OTHER PUBLICATIONS

L. Cercek and B. Cercek, "Effects of Ascorbate Ions on Intracellular Fluorescein Emission Polarization Spectra in Cancer and Normal Proliferating Cells," *Cancer Detection and Prevention* 10:1–20 (1987).

K. Suzuki and Y. Sasaki, "Studies on Encephalitogenic Fragments of Myelin Protein. IV. Synthesis of Glycine Analogs of Tryptophan–Containing Fragment," *Chem. Pharm. Bull.* 22:2181–2187 (1974).

A. A. Gershkovich et al., "A Study of the Properties of Synthetic Analogs of the Tryptophan–Containing Fragment 113–121 of the Basic Protein of Myelin," *Khim. Prirod. Soedinen,* 4:557–565 (1979).

C. M. Deber & M. E. M. Young, "Association of Carbon–13 Enriched Human Encephalitogenic Nonapeptide with a Membrane Surface," *J. Biol. Chem.* 254 6341–6345 (1979).

C. Blake & B. J. Gould, "Use of Enzymes in Immunoassay Techniques: A Review," *Analyst* 109:533–547 (1984).

M. Oellerich, "Enzyme–Immunoassay: A Review," *J. Clin. Chem. Clin. Biochem.* 22:895–904 (1984).

J. L. Marx, "How Cancer Cells Spread in the Body," *Science* 244:147–148 (1989).

B. W. Hancock & R. C. Rees, "Interleukin–2 and Cancer Therapy," *Cancer Cells* 2L 29–32 (1990).

J. G. Kaplan & C. Bona, "Proteases as Mitogens: The Effect of Trypsin and Pronase on Mouse and Human Lymphocytes," *Exp. Cell Res.* 88:388–394 (1974).

Y. Shai et al., "Antisense Peptide Recognition of Sense Peptides: Sequence Simplification and Evaluation of Forces Underlying the Interaction," *Biochemistry* 28:8804–8811 (1989).

G. Fassina et al., "Recognition Properties of Antisense Peptides to $Arg^8$–Vasopressin/Bovine Neurophysin II. Biosynthetic Precursor Sequences," *Biochemistry* 28:8811–8818 (1989).

M. R. Potter & M. Moore, "Natural Cytotoxic Reactivity of Human Lymphocyte Subpopulations," *Immunology* 37:187–194 (1979).

J. L. Marx, "What T Cells See and How They See It," *Science* 242:863–194 (1979).

W. Becker, "Determination of Antisera Titres Using the Single Radial Immunodiffusion Method," *Immunochemistry* 6:539–546 (1969).

R. W. Carrell et al., "Structure and Variation of Human $\alpha_1$–Antitrypsin," *Nature* 298:329–334 (1982).

M. Fagerhol & D. W. Cox, "The Pi Polymorphism; Genetic, Biochemical, and Clinical Aspects of Human $\alpha_1$–Antitrypsin," *Advances in Human Genetics* (H. Harris and K. Hirschhorn, eds., Plenum Press, New York, 1981), vol. 11, pp. 1–62.

W. Troll, M. S. Meyn & T. G. Rossman, "Mechanisms of Protease Action in Carcinogenesis," in *Carcinogenesis—A Comprehensive Survey, vol. II; Mechanisms of Tumor Promotion and Cocarcinogenesis* (T. J. Slaga et al., eds., Raven Press, New York 1978), pp. 301–312.

T. G. Rossman & W. Troll, "Protease Inhibitors in Carcinogenesis: Possible Sites of Action," in *Carcinogenesis, vol. V: Modifiers of Chemical Carcinogenesis* (T. J. Slaga, ed., Ravel Press, New York, 1980), pp. 127–148.

G. J. Cianciolo, "Anti–Inflammatory Effects of Neoplasia," in *Inflammation: Basic Principles and Clinical Correlates* (J. I. Gallin et al., eds., Raven Press, New York, 1988), ch. 48, pp. 861–874.

E. Reich, "Tumor–Associated Fibrinolysis," *Fed. Proc.* 32:2174–2175 (1973).

H. B. Bosmann, "Release of Specific Protease During Mitotic Cycle of L5178Y Murine Leukaemic Cells by Sublethal Autolysis," *Nature* 249:144–145 (1974).

D. Moscatelli & D. B. Rifkin, "Membrane and Matrix Localization of Proteinases: A Common Theme in Tumor Cell Invasion and Angiogenesis," *Biochim. Biophys. Acta* 948:67–85 (1988).

B. Hagmar et al., "Why Do Tumors Metastasize? An Overview of Current Research," *Tumor Biol,* 5:141–149 (1984).

C. A. McWherter et al., "Novel Inhibitors of Human Leukocyte Elastase and Cathepsin G. Sequence Variants of Squash Seed Protease Inhibitor with Altered Protease Selectivity," *Biochemistry* 28:5708–5714 (1989).

D. C. Linch et al., "Signal Transduction in Human T Lymphocytes," *Immunol. Rev.* 95:137–159 (1987).

G. L. Nicolson, "Cancer Metastasis: Tumor Cell and Host Organ Properties Important in Metastasis to Specific Secondary Sites," *Biochim. Biophys. Acta* 948:175–224 (1988).

M. S. Bernatowicz & G. R. Matsueda, "Preparation of Peptide–Protein Immunogens Using N–Succinimidyl Bromoacetate as a Heterobifunctional Crosslinking Reagent," *Anal. Biochem.* 155:95–102 (1986).

E. Harlow & D. Lane, "Antibodies: A Laboratory Manual" (Cold Spring Harbor, New York, 1988), ch. 5, pp. 53–137.

J. W. Goding, "Monoclonal Antibodies: Prinicples and Practice" (Academic Press, London, 2d ed., 1986), pp. 59–141.

P. Tijssen, "Practice and Theory of Enzyme Immunoassays" (Elsevier, Amsterdam, 1985), pp. 297–314.

C. Wittekind et al., "Localization of CEA, HCG, Lysozyme, Alpha–1–Antitrypsin, and Alpha–1–Antichymotrypsin in Gastric Cancer and Prognosis," *Virchows Arch. A:* 409:715–724 (1986).

H. Kataoka et al., "Neutral Proteinases and Inhibitors Secreted by Human Rectal Adenocarcinoma Cell Line (RCM–1)," *Invasion Metastasis* 9:149–166 (1989).

H. Kataoka et al., "New Human Colorectal Carcinoma Cell Lines That Secret Proteinase Inhibitors in Vitro," *Virchows Archiv B* 57:157–165 (1989).

R. G. Crystal, "$\alpha$1–Antitrypsin Deficiency, Emphysema, and Liver Disease," *J. Clin. Invest.* 85:1343–1352 (1990).

R. W. Carrell et al., "The Molecular Pathology of the Serpins," *Mol. Biol. Med.* 6:35–42 (1989).

G. L. Long et al., "Complete Sequence of the cDNA for Human $\alpha_1$–Antitrypsin and the Gene for the S Variant," *Biochemistry* 23:4828–4837 (1984).

C. Longstaff & P. J. Gaffney, "Serpin–Serine Protease Binding Kinetics: $\alpha_2$–Antiplasmin as a Model Inhibitor," *Biochemistry* 23:4828–4837 (1984).

A. E. Mast et al., "Analysis of the Plasma Elimination Kinetics and Conformational Stabilities of Native, Proteinase–Complexed, and Reactive Site Cleaved Serpins: Comparison of $\alpha_1$–Proteinase Inhibitor, $\alpha$–Antichymotrypsin, Antithrombin III, $\alpha_2$–Antiplasmin, Angiotensinogen, and Ovalbumin," *Biochemistry* 30: 1723–1730 (1991).

D. H. Perlmutter et al., "Endocytosis and Degradation of $\alpha_1$–Antitrypsin–Protease Complexes is Mediated by the Serpin–Enzyme Complex (SEC) Receptor", *J. Biol. Chem.* 265:16713–16713 (1990).

I. Wilson et al., "The Structure of an Antigenic Determinant in a Protein," *Cell* 37:767–778 (1984).

M. Bodanszky, "Peptide Chemistry: A Practical Textbook" (Springer–Verlag, Berlin, 1988), ch. 10, pp. 147–168.

T. E. Creighton, "Proteins: Structures and Molecular Properties" (W. H. Freeman, New York, 1984) pp. 110–112.

F. M. Burnet, "The Concept of Immunological Surveillance," *Prog. Exp. Tumor Res.* 13:1–27 (1970).

R. B. Herberman, "Possible Roles of Natural Killer Cells and Other Effector Cells in Immune Surveillance Against Cancer," *J. Invest. Dermatol.* 83:137S–140S (1984).

L. M. Muul et al., "Large Scale Production of Human Lymphokine Activated Killer Cells for Use in Adoptive Immunotherapy," *J. Immunol. Meth.* 88:265–275 (1986).

T. L. Whiteside, "Human Tumor–Infiltrating Lymphocytes and Their Characterization," in *Interleukin–2 and Killer Cells in Cancer* (E. Lotzova & R. B. Herberman, eds., CRC Press, Boca Raton, Florida, 1990) pp. 133–151.

R. Snyderman & G. J. Ciancolo, "Immunosuppressive Activity of the Retroviral Envelope Protein P15E and its Possible Relationship to Neoplasia," *Immunol. Today* 5:240–244 (1984).

S. C. Chow & M. Jondal, "A Central Role for Phosphoinositide Hydrolysis in Activating the Lytic Mechanism of Natural Killer Cells," *Immunology* 70: 106–110 (1990).

D. Hudig et al., "Active Tumor Cell Resistance to Human Natural Killer Lymphocyte Attack," *Cancer Res.* 41:2803–2808 (1981).

M. Sarzotti et al., "EL–4 Metastases in Spleen and Bone Marrow Suppress the NK Activity Generated in these Organs," *Int. J. Cancer* 39:118–125 (1987).

K. M. Rigg et al., "Alterations in Circulating Lymphocyte Number and Function After Circulation Through Colorectal Carcinoma," *Surgery* 109:747–755 (1991).

H. Kumagawa & M. Hess, "Influence of Serum Derived from Patients with Head and Neck Cancer on Natural Killer Activity," *Oncology* 48:372–376 (1991).

M. Moore & B. M. Vose, "Extravascular Natural Cytotoxicity in Man: Anti–K562 Activity of Lymph–Node and Tumour–Infiltrating Lymphocytes," *Int. J. Cancer* 27:265–272 (1981).

E. H. Steinhauer et al., "Defective Natural Cytotoxicity in Patients with Cancer: Normal Number of Effector Cells but Decreased Recycling Capacity in Patients with Advanced Disease," *J. Immunol . . .* 129:2255–2259 (1982).

R. A. Mickel et al., "Natural Killer Cell Cytotoxicity in the Peripheral Blood, Cervical Lymph Nodes, and Tumor of Head and Neck Cancer Patients," *Cancer Res.* 48–5017–5022 (1988).

G. Smithson et al., "The Role of NK Cells in the Regulation of Experimental Metastasis in a Murine Lymphoma System," *J. Leukocyte Biol.* 49:621–629 (1991).

S. A. Rosenberg et al., "Experience with the Use of High–Dose Interleukin–2 in the Treatment of 652 Cancer Patients," *Ann. Surg.* 210: 474–484 (1989).

S. A. Rosenberg et al., "Use of Tumor–Infiltrating Lymphocytes and Interleukin–2 in the Immunotherapy of Patients with Metastatic Melanoma: A Special Report," *New Eng. J. Med..* 319:1676–1680 (1988).

J. Banchereau & F. Rousset, "Growing Human B Lymphocytes in the CD40 System," *Nature* 353:678–679 (1991).

E. S. Golub & D. R. Green, "Immunology A Synthesis" (2d ed., Sinauer Associates, Sunderland, Mass., 1991), pp. 143–147 & 575–595.

B. D. Davis et al., "Microbiology" (4th ed., J. B. Lippincott, Philadelphia, 1990), pp. 499–500.

D. N. Posnett et al., "A Novel Method for Producing Anti–Peptide Antibodies," *J. Biol. Chem.* 283:1719–1725 (1988).

METHODS AND PHARMACEUTICAL COMPOSITIONS FOR BLOCKING SUPPRESSION OF IMMUNE DEFENSE MECHANISMS USING AN ANTIBODY, A FACTOR, OR AN ANTISENSE PEPTIDE

CROSS-REFERENCES

This application is a continuation-in-part of application Ser. No. 07/539,686, filed Jun. 18, 1990, (now U.S. Pat. No. 5,270,171, issued Dec. 14, 1993) and entitled "Cancer-Associated SCM-Recognition Factor, Preparation and Method of Use," which is a continuation-in-part of Ser. No. 07/167,007, filed Mar. 3, 1988, entitled "General Cancer-Associated SCM-Recognition Factor, Preparation and Method of Use," and now abandoned, which itself was a continuation-in-part of Ser. No. 07/022,759, filed Mar. 6, 1987, also entitled "General Cancer-Associated SCM-Recognition Factor, Preparation and Method of Use," and also now abandoned. All of these applications are by Dr. Boris Cercek and Dr. Lea Cercek, and are incorporated herein by this reference. This application is also related to several prior patent applications, all by Drs. Boris & Lea Cercek: (1) Ser. No. 06/838,264, filed Mar. 10, 1986 (now abandoned), and Ser. No. 07/260,928, filed Oct. 21, 1988, ( now U.S. Pat. No. 5,260,186, issued Nov. 9, 1993) a continuation-in-part of Ser. No. 06/838,264, both entitled "Provision of Density Specific Blood Cells for the Structuredness of the Cytoplasmic Matrix (SCM) Test"; and (2) Ser. No. 06/867,079, filed May 27, 1986 (now abandoned), and Ser. No. 07/222,115, filed Jul. 20, 1988, a continuation-in-part of Ser. No. 06/867,079 (now U.S. Pat. No. 5,166,052, issued Nov. 24, 1992), both entitled "Method for Measuring Polarization of Bathochromically Shifted Fluorescence." The disclosures of these related patent applications are incorporated herein by this reference.

BACKGROUND

This invention is directed to methods and compositions for prevention of immune defense suppression and augmenting natural defenses to cancer.

Despite nearly a century of intensive basic and clinical research, cancer remains one of the most dreaded diseases, still claiming hundreds of thousands of victims per year in the United States alone. Over the last few years, much work has been directed toward improving the body's natural defenses against cancer. The ability of certain lymphocytes to kill cancer cells is known generally as immune defense. See, generally, E. S. Golub and D. R. Green, "Immunology: A Synthesis" (Sinauer Associates, Sunderland, Nass.) 2d ed., 1991, Ch. 33, pp. 575–595, incorporated herein by this reference. Among the therapeutic methods intended to increase immune defense and thereby bolster the body's own defenses against cancer has been the administration of lymphokines such as interleukin-2 (IL-2), tissue necrosis factor α (TNFα), and interferons. Although it can be shown that these agents, when administered in vitro are capable of stimulating both natural killer (NK) and lymphokine-activated killer (LAK) activity, the use of lymphokines and/or other agents intended to stimulate natural immunity towards tumor cells has yielded erratic clinical results. (Mesler et al., "Large Scale Production of Human Lymphokine Activated Killer Cells for Use in Adoptive Immuno Therapy," *J. Immunol. Meth.* 88:265–275 (1986); T. L Whiteside, "Human Tumor-Infiltrating Lymphocytes and Their Characterization," in Interleukin-2 and Killer Cells in Cancer, Ch. 10, pp. 133–151; B. W. Hancock & R. C. Rees, "Interleukin-2 and Cancer Therapy," *Cancer Cells* 2:29–32 (1990)). Because lymphokines can produce serious side effects when used in high doses, there exists a need for a method of potentiating the effect of lymphokines and other immune-surveillance-stimulating agents in vivo in order to consequences of excessively high doses of these agents. Such a method would greatly improve cancer treatment and could be used in conjunction with other cancer therapies, such as radiation or chemotherapy. Such therapy also might prove of value in treatment of neoplasms in immunologically compromised individuals, such as those infected with the HIV virus, in whom cancers such as Kaposi's sarcoma, non-Hodgkin's lymphoma, and various carcinomas, frequently occur. There is thus a need to develop a more efficient method of immune defense that can assist the body in fighting cancer without excessively high and toxic doses of lymphokines.

It has been suggested that cancer cells may have defense mechanisms, which enable them to evade immune defense and resist or inactivate the cytolytic action of NK and LAK lymphocytes (R. Snyderman & G. J. Cianciolo, "Immunosuppressive Activity of the Retroviral Envelope Protein p15E and Its Possible Relationship to Neoplasia," in *Immunology Today* (J. Inglis, ed., Elsevier, Amsterdam, 1984). There is therefore a need for a method of blocking or reversing the defense mechanisms of cancer cells that allow them to evade immune defense by lymphocytes.

SUMMARY

We have developed methods of preventing the suppression of immune defense caused by SCM-factor peptides. Such methods are useful in the treatment of malignancies and can be utilized along with other treatments, such as radiation, surgery, and chemotherapy.

Methods according to the present invention block suppression of at least one of the natural killer (NK) and lymphokine-activated killer (LAK) immune defense mechanisms.

One method according to the present invention is based on the ability of agents such as antibodies, antisense peptides, and a high-molecular-weight blood plasma factor to scavenge, inactivate, or eliminate SCM-factor peptides from the blood plasma. This allows the lymphocytes to express immune defense activities such as NK or LAK.

In general, the method of the present invention comprises administering to a cancer patient an agent capable of blocking the immune defense suppressive activities of an SCM-factor peptide in a quantity sufficient to block suppression of at least one of the natural killer (NK) and lymphocyte activated killer (LAK) immune defense mechanisms.

In one embodiment, the agent is an antibody; the antibody can be a monoclonal antibody. Preferably, the antibody is autologous for the patient to which it is administered. Such an autologous antibody can be produced by the culture in vitro of autologous B lymphocytes producing antibodies capable of blocking the immune defense suppressive activities of the SCM-factor peptide.

Preferably, the antibody is administered in a quantity sufficient to bind substantially all of the SCM-factor peptide present in the blood plasma.

Antibodies useful for the method of the present invention include antibodies that specifically binds a domain of the SCM-factor peptide, the domain being selected from the group consisting of F-N-K-P-F-V-F-L-M-I-D-Q-N-T-K-V-

P-L-F-M-G-K (SEQ ID NO: 1) and a domain related thereto by one or more conservative amino acid substitutions. Alternatively, the antibody can bind a domain selected from the group consisting of F-L-M-I-D-Q-N-T-K-V-P-L-F-M-G-K (SEQ ID NO: 2) and a domain related thereto by one or more conservative amino acid substitutions.

In another alternative, the agent used for blocking the suppression of immune defense can comprise a factor present in autologous, cell-free blood plasma and substantially removed by ultrafiltration through a filter with a nominal molecular weight cutoff of 50 kD.

In still another alternative, the agent used for blocking suppression of immune defense can comprise an antisense peptide whose amino acid sequence is encoded by the antisense strand of a DNA sequence whose sense strand encodes a domain of the SCM factor, the domain having a sequence such that antibodies capable of binding specifically to the domain block the immune defense suppressive effect of SCM factor.

The blockage of suppression of immune defense can comprise a stimulation of synthesis and/or release of at least one humoral factor selected from the group consisting of interleukin-2 (IL-2) and tissue necrosis factor α (TNFα). When the synthesis and/or release of at least one humoral factor is stimulated, the method can further comprise the step of determining the degree of blockage of suppression of immune defense by monitoring an increase in synthesis and/or release of the at least one humoral factor.

This treatment method can further comprise the step of administering to the patient at least one humoral factor capable of stimulating at least one of the NK and LAK activities. Typically, the humoral factor is selected from the group consisting of IL-2 and TNFα.

Another aspect of the present invention is a method of inducing production in a mammal of antibodies specifically binding an SCM-factor peptide. The method comprises immunizing the mammal with at least one conjugate selected from the group consisting of:

(1) a peptide selected from the group consisting of a peptide of the sequence F-L-M-I-D-Q-N-T-K-V-P-L-F-M-G-K-C (SEQ ID NO: 3) and peptides related thereto by one or more conservative amino acid substitutions conjugated at its carboxy-terminal cysteine residue to a carrier protein;

(2) a peptide selected from the group consisting of a peptide of the sequence F-N-K-P-F-V-F-L-M-I-D-Q-N-T-K-V-P-L-F-M-G-K-C (SEQ ID NO: 4) and peptides related thereto by one or more conservative amino acid substitutions conjugated at its carboxy-terminal cysteine residue to a carrier protein; and (3) a macromolecular aggregate composed of multiple copies of peptides selected from the group consisting of:

(a) a peptide selected from the group consisting of a peptide of the sequence F-L-M-I-D-Q-N-T-K-V-P-L-F-M-G-K-C (SEQ ID NO: 3) and peptides related thereto by one or more conservative amino acid substitutions;

(b) a peptide selected from the group consisting of a peptide of the sequence F-N-K-P-F-V-F-L-M-I-D-Q-N-T-K-V-P-L-F-M-G-K-C (SEQ ID NO: 4) and peptides related thereto by one or more conservative amino acid substitutions;

(c) a peptide selected from the group consisting of a peptide of the sequence F-N-K-P-F-V-F-L-M-I-D-Q-N-T-K-V-P-L-F-M-G-K (SEQ ID NO: 1) and peptides related thereto by one or more conservative amino acid substitutions; and (d) a peptide selected from the group consisting of a peptide of the sequence F-L-M-I-D-Q-N-T-K-V-P-L-F-M-G-K (SEQ ID NO: 2) and peptides related thereto by one or more conservative amino acid substitutions. The macromolecular aggregate of (3) is formed without conjugation to a carrier protein.

This immunization method can be used to produce antibodies in a human subject to produce antibodies to scavenge SCM-factors in the body fluids of the immunized subject.

Another aspect of the present invention is a pharmaceutical composition comprising:

(1) an agent capable of blocking the immune defense suppressive effect of a SCM-factor peptide in a quantity sufficient to block suppression of immune defense in a patient with cancer; and (2) a pharmaceutically acceptable carrier.

Still another aspect of the present invention is a kit for stimulating immune response of a cancer patient, comprising, in separate containers:

(1) the pharmaceutical composition described above; and (2) a composition comprising:

(a) a lymphokine capable of stimulating at least one of the natural killer (NK) and lymphokine activated killer (LAK) immune defense mechanisms in a quantity sufficient to stimulate immune defense; and (b) a pharmaceutically acceptable carrier.

Optionally, the kit can further comprise an inhibitor of protein synthesis with specific effects on tumor cells. A preferred inhibitor is ascorbic acid.

BRIEF DESCRIPTION OF THE DRAWINGS

These and other features, aspects, and advantages of the present invention will become better understood with reference to the following description, appended claims, and the accompanying drawings where:

DEFINITIONS

Figure 1:
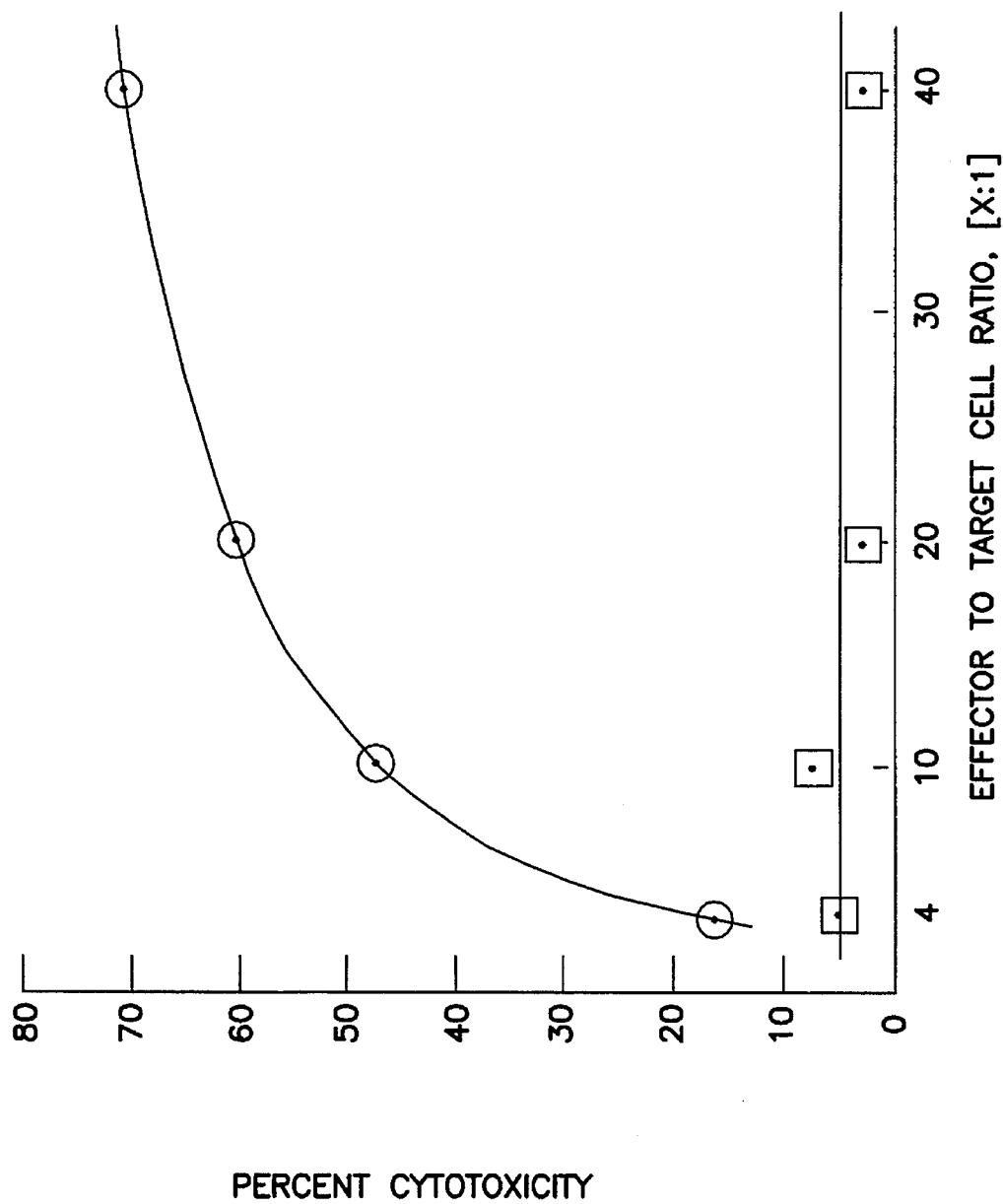
FIG. 1 is a graph showing the effect of lymphocyte to target cell ratios on the extent of natural killer (NK) cytotoxicity before and after treatment of the lymphocytes with SCM-factor peptide.

Definitions for a number of terms which are used in the following Description, Examples, and appended claims are collected here for convenience.

"General": Nonspecific with respect to the particular type of cancer afflicting either the donor of the body fluid from which a particular SCM factor is purified, or the donor of the lymphocytes used with that factor in the SCM test.

"Fluorogenic Agent Precursor": A nonfluorogenic compound capable of being taken up by lymphocytes and converted intracellularly by hydrolysis into a fluorogenic compound, of which the example used herein is fluorescein diacetate (FDA).

"Standard SCM Test": An SCM test using 1.0 ml of a lymphocyte suspension at $6 \times 10^6$ cells/ml and 0.1 ml of the cancer recognition factor or mitogen, with FDA as the fluorogenic agent precursor and using an excitation wavelength of 470 nm and an emission wavelength of 510 nm for fluorescence polarization measurements.

"Apparent Molecular Weight" and "Nominal Molecular Weight Cutoff": Both of these terms refer to the fact that the separation of molecules by ultrafiltration according to size is approximate for molecules in the size range of SCM factor, and depends on conformation as well as size. Thus an ultrafilter with a nominal molecular weight cutoff of x daltons will separate molecules with an apparent molecular weight of less than x daltons from molecules with an apparent molecular weight greater than x daltons. However, some molecules with an actual molecular weight greater than x daltons will pass through such a filter.

"Substantially Pure Cancer Recognition Factor": Material exhibiting cancer recognition activity as determined in the SCM test and of such a state of purity that at least about 95% of other molecules with specific biological activity, including all proteins and larger peptides, is not present in the material. The term "substantially purified" refers to the same state of purity.

"SCM-Factor Peptide": A peptide, either natural or synthetic, exhibiting cancer recognition activity as determined in the SCM test.

"Tryptic Peptide": A peptide cleaved from a larger peptide by the action of the proteolytic enzyme trypsin, which breaks peptide chains after lysine or arginine residues.

"Partially Homologous": Two peptide or protein sequences are partially homologous when there exists a degree of residue-to-residue correspondence between the two sequence greater than about 40%, i.e., substantially greater than expected by chance.

"Immune Defense": The term "immune defense," as used herein, refers to lymphocyte-mediated cytotoxicity directed against cancer cells, and includes both natural killer (NK) activity and lymphokine-activated killer (LAK) activity.

"Block": The term "block," as used herein to refer to suppression of immune defense, includes not only blockage of suppression of immune defense, but reversal of that suppression. This includes blockage or reversal of suppression brought about by suppression of synthesis of SCM-factor peptides in cancer cells.

DESCRIPTION

We have unexpectedly found that peptides active in the assay known as the structuredness of the cytoplasmic matrix (SCM) test (SCM-factor peptides) can produce suppression of immune defense, and that this suppression of immune defense can be inhibited by agents that block this activity of the SCM-factor peptides.

The SCM test was first developed by the present inventors as a means of detecting cancer. The test was based on the finding that certain factors, known generically as SCM factors, are capable of causing a decrease in the structuredness of the cytoplasmic matrix (SCM) when lymphocytes from cancer patients are incubated with the factors. This decrease does not occur when lymphocytes from patients free of cancer are incubated with the factors. The decrease in the structuredness of the cytoplasmic matrix is typically detected by a decrease in the fluorescence polarization of a nonfluorescent fluorogenic agent precursor taken up by the cells and converted to a fluorescent compound by hydrolysis in the cells. The performance of the SCM test is described in detail in L. Cercek & B. Cercek, "Application of the Phenomenon of Changes in the Structuredness of the Cytoplasmic Matrix (SCM) in the Diagnosis of Malignant Disorders: A Review," *Eur. J Cancer* 13:903–915 (1977), incorporated herein by this reference.

In our copending application, U.S. application Ser. No. 07/539,686, filed Jun. 18, 1990 and entitled "Cancer-Associated SCM-Recognition Factor, Preparation and Method of Use," incorporated herein by this reference, we reported the isolation of a number of SCM factors from blood plasma of patients with various types of cancer. The isolated SCM factors are peptides of 29 to 35 amino acids in length and have substantial homology in their amino acid sequences. One region of nine amino acids, from residues 14 to 22, is substantially invariant in the isolated SCM factors. Based on these sequences, we synthesized a synthetic SCM factor with a consensus sequence of 29 amino acid residues, which was fully active in the SCM test.

As detailed below, the suppression of immune defense by SCM-factor peptides can be inhibited by a number of agents, including antibodies to either intact SCM-factor peptides or to the region of the SCM factor responsible for suppressing immune defense, a high-molecular-weight factor present in blood plasma, and antisense peptides corresponding to SCM-factor peptides. Accordingly, the present invention encompasses methods for inhibition of suppression of immune defense caused by SCM-factor peptides, methods for treatment of cancer based on inhibition of suppression of immune defense and/or on suppression of synthesis of SCM-factor peptides in cancer cells using non-toxic drugs, pharmaceutical compositions suitable for use in such methods, and kits comprising the pharmaceutical compositions together with a separately packaged NK/LAK augmenting lymphokine, and, optionally, with a separately packaged drug for suppression of SCM-factor synthesis in tumor cells.

I. ISOLATED AND PURIFIED GENERAL CANCER-ASSOCIATED SCM-RECOGNITION FACTORS

The general cancer-associated SCM-recognition factor was isolated and purified to homogeneity from blood plasma obtained from patients with twelve different types of cancer. As detailed below, these peptides all are either 29 or 35 amino acids in length and are substantially homologous in amino acid sequence.

A. Purification

The purification of the SCM-recognition factor to substantial homogeneity from blood plasma was performed as described in U.S. patent application Ser. No. 07/167,007 by Drs. Boris and Lea Cercek, entitled "General Cancer-associated SCM-recognition Factor, Preparation and Method of Use" and incorporated herein by this reference. The purification process preferably occurs in five steps: (1) ultrafiltration; (2) desalting; (3) gel filtration; (4) anion-exchange chromatography; and (5) reverse-phase high-pressure liquid chromatography (RP-HPLC).

1. Ultrafiltration

The first step in purification of the SCM factor is obtaining an ultrafiltrate from a body fluid of a donor afflicted with cancer. The body fluid can be peripheral blood, blood plasma, or urine; if the fluid is peripheral blood, the blood is centrifuged to separate the red blood cells from the plasma. The donor of the body fluid used for isolation of the SCM factor can be either autologous or allogeneic with respect to the lymphocytes used for the SCM test. Alternatively, the SCM factor can be purified from cell aspirates or other cellular materials derived from patients with malignancies.

The ultrafiltration process separates the first fraction of the body fluid comprising molecules having an apparent molecular weight greater than 1,000 daltons from a second fraction comprising molecules having an apparent molecular weight less than 1,000 daltons. The general cancer-associated SCM factor of the present invention is found in the second fraction of the ultrafiltrate. The terms "apparent molecular weight" and "nominal molecular weight cutoff" are used herein because ultrafiltration is a somewhat imprecise method of separating molecules according to molecular weight in this molecular weight range, and the exact molecular weight excluded by a filter with a nominal molecular weight cutoff of 1,000 daltons depends somewhat on the conformation of the molecule. Molecules larger than 1,000 daltons in actual molecular weight can, in fact, pass through an ultrafilter with a nominal molecular weight cutoff of 1,000 daltons if, for example, the molecules are relatively long and narrow. In fact, the purified general cancer-associated SCM factors of the present invention are either 29 or 35 amino acids long and have molecular weights of approximately 3,200 or 3,900 daltons, respectively. Nevertheless, all of these peptides pass through an ultrafilter with a nominal molecular weight cutoff of 1,000 daltons.

Preferably, the separation of the second fraction from the first fraction is performed by filtration of the body fluid through an ultrafilter with a nominal 1,000-dalton molecular weight cutoff, such as, but not limited to, an Amicon™ UM2 or YM2 filter (available from Amicon Corporation, Scientific System Division, Danvers, Mass. 01923).

The purity of a preparation of such a factor, at the ultrafiltrate stage or later, can be described by its specific activity. In this context, the term "specific activity" is defined as the reciprocal of the quantity of protein required to cause a particular degree of decrease, such as 20%, in the intracellular fluorescence polarization value when a particular fraction is used to challenge SCM-responding lymphocytes in the SCM test. The goal of purification of the SCM factor is to increase the specific activity of the SCM factor over the specific activity found in the crude ultrafiltrate. The process of purification can therefore be followed by determining the specific activity of the purified fractions at each stage. Since the protein concentration in the examples reported herein is only determined approximately in terms of ultraviolet absorbance, preferably at 220 nm, and the complete dose-response curve for the factor has not yet been determined, the characterization of various steps of the purification of the SCM factor described herein in terms of specific activity is only approximate. However, it is clear that the protein concentration decreases markedly as the factor moves through the various purification steps while the activity of the factor is relatively unaffected, thereby resulting in an increase in specific activity of the SCM factor. Nevertheless, even the ultrafiltrate can properly be described as consisting essentially of substantially purified general cancer-associated SCM-recognition factor, inasmuch as ultrafiltration through a membrane with a nominal molecular weight cutoff of 1,000 daltons removes from a biological fluid the overwhelming majority of molecules with any biological activity, including all proteins and larger peptides.

2. Desalting

The next step in the purification of the general cancer-associated SCM factor is a desalting step in which the fraction obtained from ultrafiltration is loaded on a chromatographic column capable of separating the salts therefrom. The material loaded onto the column is then eluted from the column with distilled water, and the portion eluting at an elution volume of between about 0.3 and about 0.5 times the total chromatographic bed volume, containing the SCM factor, is collected. Preferably, the column used in this step is a gel-filtration column with a fractionation range of from 0 to about 700 daltons, such as Sephadex™ G-10 (Pharmacia, Uppsala, Sweden), a dextran gel. A polyacrylamide gel with corresponding separation characteristics can also be used.

3. Gel Filtration

The next step in the purification is another gel filtration step, again separating according to size. The SCM-containing material obtained from the desalting step is loaded onto another gel filtration column with a fractionation range of from about 1,500 to about 30,000 daltons. Preferably, the gel filtration column material is a dextran such as Sephadex™ G-50, but a corresponding polyacrylamide gel can also be used. The material loaded onto the column is then eluted therefrom with a weak aqueous solution of an ammonium salt. Preferably, the ammonium salt is ammonium bicarbonate, more preferably 50 mM ammonium bicarbonate. That portion eluting at an elution volume between about 0.4 times and about 0.6 times the total chromatographic bed volume contains the SCM factor and is collected.

4. Anion-Exchange Chromatography

The next step in the purification is an anion-exchange chromatography step, separating by charge. The SCM factor-containing material from the previous gel filtration step is loaded onto an anion exchange column, preferably diethylaminoethyl-cellulose (DEAE-cellulose). The material loaded onto the column is then eluted therefrom with an increasing concentration of an ammonium salt. Preferably, the ammonium salt is ammonium bicarbonate and the increasing concentration of the ammonium salt is from 10 mM to 1.0M ammonium bicarbonate. The fraction eluting from the column at about 0.28M to 0.31M ammonium bicarbonate contains the SCM factor and is collected.

5. Reverse-Phase High-Pressure Liquid Chromatography

The final step of purification is reverse-phase high-pressure liquid chromatography (RP-HPLC), which separates by charge and/or hydrophobicity. Typically, the SCM factor-containing material from the DEAE-cellulose column eluate is loaded onto an Aquapore™ RP-300 RP-HPLC column with dimensions of 220 mm×2.1 mm. Elution is then performed with a combination of two solvents: initially, 90 volume percent of 0.1 volume percent aqueous trifluoroacetic acid (TFA) (solvent A) and 10 volume percent of 0.09 volume percent of TFA in aqueous 70% acetonitrile (solvent B), followed by a gradient with an increasing concentration of solvent B. The SCM factor from all starting materials elutes as an homogeneous peak at a solvent composition of 26 volume percent solvent A and 74 volume percent solvent B.

Alternatively, RP-HPLC can be performed on a Beckman Instruments Ultrasphere ODS™ column. With this column, elution is then performed with a somewhat different solvent pattern, initially 70 volume percent of solvent A and 30 volume percent of 0.1 volume percent aqueous TFA in aqueous 70% acetonitrile (solvent C), followed by a gradient with an increasing concentration of solvent C. The SCM factor always elutes as an homogeneous peak at a solvent composition of 43.7 volume percent of solvent A and 56.3 volume percent of solvent C when the Ultrasphere column and this solvent system is used.

B. Structure of the Isolated Cancer-Associated SCM-Recognition Factor

The amino acid sequences of the SCM factors isolated from blood plasmas from patients with 12 different types of cancer have been determined by sequential Edman degradation. The results are reported in Example 6, below. Certain residues are unidentified; these residues are likely cysteine and are reported herein as such. In nine out of the twelve cancers, the SCM factor was 29 amino acids long; in the remaining three, an additional six amino acids were present, yielding a total of 35 amino acids. In seven of twelve of the factor preparations, polymorphisms exist, in that there are conservative substitutions at one or two positions of the peptide. In these cases, the preparation contains two amino acids as identified by Edman degradation at one or two positions of the peptide. There are never more than two such substitutions. Also, in two cases, gastric sarcoma and prostate cancer, the SCM factor appears in two forms, one of 29 amino acid residues and the other of 35 amino acid residues. No forms of intermediate length are found. For seminoma of the testes, only the 35 amino acid form is found. These slight differences in amino acid sequence do not affect the cross-reactivity of the factors in the SCM test.

One region of the sequence is nearly invariant—residues 14–22. This sequence is F-L-M-I-D-Q-N-T-K (SEQ ID NO: 5), except in the factors for prostate cancer and seminoma of the testes, in which E (glutamate) replaces D (aspartate) at position 18. This change is extremely conservative, inasmuch as glutamate and aspartate have the same charge and differ by only one methyl group. This region is believed to be extremely significant for the functioning of the SCM factor, as discussed below.

C. Properties of the Isolated, Purified General Cancer-Associated SCM-Recognition Factor 1. Activity in the SCM Test The purified SCM factors are fully active in the SCM test when used as a challenging agent for lymphocytes isolated from patients with several different types of malignancies. This activity can be demonstrated by assay at any point during the purification of the factor, starting at the ultrafiltrate. Details of the results of such assays are given below under "Examples." The greatest activity is obtained with material taken from the final RP-HPLC step. One-tenth milliliter of this fraction, having an approximate protein content of 40 picomoles of peptide, causes a decrease in intracellular fluorescence polarization of as much as 44.6% when used to challenge SCM-responding lymphocytes isolated from cancer patients, but causes no decrease in intracellular fluorescence polarization when used to challenge the same population of lymphocytes isolated from healthy donors.

2. Tryptic Peptides of the Factors

Purified preparations of the SCM factor from plasma of patients with lung cancer and breast cancer were subjected to tryptic digestion, followed by purification of the tryptic peptides by RP-HPLC. In each case, a particular fragment eluted at 30.4 volume percent of solvent A and 69.6 volume percent of solvent B, in RP-HPLC using the Aquapore™ RP-300 column. These fractions were found, by sequence analysis, to be the fragment of the SCM factor consisting of residues 8–22. (In both cases, residue 7 is lysine, and trypsin is known to cleave after lysine residues.)

These tryptic peptides are fully active in the SCM test (Example 5). Approximately $5 \times 10^{-2}$ femtograms of the tryptic peptide from the SCM factor isolated from plasma from patients with lung cancer (the lung cancer SCM factor), which is approximately 16,000 molecules, gave full activity in the SCM test when used as challenging agent for lymphocytes from donors with cancer. The fragment from the lung cancer SCM factor reacted equally well with lymphocytes from donors with lung cancer and breast cancer, but caused no response in the SCM test when used to challenge lymphocytes from normal donors. Further details are given below under "Examples." Significantly, both tryptic fragments include the nearly invariant region of the peptide from amino acids 14–22.

3. Cross-Reactivity of the SCM Factor

The SCM factors isolated above are designated as general cancer-associated SCM-recognition factors because lymphocytes isolated from donors with all types of cancer respond to all preparations of the factor in the SCM test. The type of cancer afflicting the donor of the lymphocytes need not be the same as the type of cancer afflicting the donor of the body fluid from which the SCM factor was purified.

4. Synthesis of SCM Factors by Cancer Cells in Culture

Metabolically active human cancer cells grown in culture, including T10806 fibrosarcoma cells, MCF7 breast cancer cells, A2780 ovarian cancer cells, and HCT80 colon cancer cells, excreted into serum-free tissue culture media molecules that, when taken through the SCM factor purification process, exhibited optical density peaks with retention times identical to those for SCM factor itself.

II. SYNTHETIC CANCER-ASSOCIATED SCM-RECOGNITION FACTOR

In view of the high degree of sequence homology between the SCM factors isolated from 12 different types of cancer, a synthetic SCM factor has now been prepared using standard solid-phase peptide synthesis methods. This synthetic SCM factor has a "consensus" sequence of 29 amino acids and shares the properties and activity of the isolated purified SCM factors.

The preparation of a synthetic SCM factor is desirable for a number of reasons: (1) availability and quantity without the necessity of isolation from cancer tissues; (2) uniformity of structure and activity; and (3) the possibility of varying the sequence in order to determine structure-activity relationships.

A. Sequence of the Synthetic SCM Factor Molecule

The synthetic SCM factor has the amino acid sequence M-I-P-P-E-V-K-F-N-K-P-F-V-F-L-M-I-D-Q-N-T-K-V-P-L-F-M-G-K (SEQ ID NO: 6).

This sequence is not the only sequence with 29 amino acids believed to possess SCM activity. It is a well-established principle of protein and peptide chemistry that certain amino acids substitutions, entitled "conservative" amino acid substitutions, can frequently be made in a protein or a peptide without altering either the confirmation or the function of the protein or peptide. Such changes include substituting any of isoleucine (I), valine (V), and leucine (L) for any other of these amino acids; aspartic acid (D) for glutamic acid (E) and vice versa; glutamine (Q) for asparagine (N) and vice versa; and serine (S) for threonine (T) and vice versa.

In view of these likely equivalencies, peptides of the sequence M-$X_2$-P-P-$X_5$-$X_6$-K-F-$X_9$-K-P-F-$X_{13}$-F-$X_{15}$-M-$X_{17}$-$X_{18}$-$X_{19}$-$X_{20}$-$X_{21}$-K-$X_{23}$-P-$X_{25}$-F-M-G-L, in which: $X_2$, $X_6$, $X_{13}$, $X_{15}$, $X_{17}$, $X_{23}$, and $X_{25}$ can each be I, L, or V; $X_5$ and $X_{18}$ can each be D or E; $X_9$, $X_{19}$ and $X_{20}$ can each be Q or N; and $X_{21}$ can be S or T, are expected to have SCM factor activity. In this designation of the sequence, and corresponding designations elsewhere employing subscripts, the number appearing in the subscript indicates the position of the amino acid specified in a factor of 29 amino acids. For example, "$X_2$" refers to the second amino acid from the amino-terminus.

The above-mentioned substitutions are not the only amino acid substitutions that can be considered "conservative." Other substitutions can also be considered conservative, depending on the environment of the particular amino acid. For example, glycine (G) and alanine (A) can frequently be interchangeable, as can be alanine and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered "conservative" in particular environments.

B. Properties of the Synthetic SCM Factor

1. Activity in the SCM Test

The synthetic SCM factor molecule is highly active in the SCM test. As little as 2 femtomoles ($2\times10^{-15}$ moles) of the synthetic SCM factor molecule produced a significant, 20%, decrease in intracellular fluorescence polarization in the SCM test when used to challenge SCM-responding lymphocytes. The synthetic peptide is active in the SCM test when used to challenge SCM-responding lymphocytes from donors with tumors of different histological type and in different organs. The corresponding fraction of SCM-responding lymphocytes from normal, healthy donors does not respond to the SCM factor in quantities as large as 960 picomoles ($960\times10^{-12}$ moles).

2. Induction of SCM-Recognition Receptors in Lymphocytes from Healthy Donors

The synthetic SCM factor can modify the SCM response of lymphocytes from healthy donors from the response characteristic of such lymphocytes (i.e., a response to PHA and no response to a cancer-associated factor) to the response characteristic of lymphocytes from donors with cancer (i.e., no response to PHA and a response to a cancer-associated factor). This property of the synthetic SCM factor is disclosed in detail in our copending application Ser. No. 07/539,686, incorporated herein by reference.

The induction of these receptors requires protein synthesis. When the incubation is carried out in the presence of the protein synthesis inhibitors cycloheximide or actinomycin D at 10 μg/$5\times10^6$ cells, no response to synthetic SCM factor was induced, and the normal response to the mitogen PHA was not abolished.

C. Production and Activity of Fragments of Synthetic SCM Factor

1. Sequences and Activity of Fragments

In order to determine which portion or portions of the synthetic SCM factor is responsible for its activity in the SCM test, five peptide fragments of the synthetic SCM factor were synthesized, designated F1 through F5. These represented the following portions of the intact molecules: F1, amino acids 1–22; F2, amino acids 8–29; F3, amino acids 8–22; F4, amino acids 14–22; and F5, amino acids 1–13. These fragments have the following amino acid sequences:

F1: M-I-P-P-E-V-K-F-N-K-P-F-V-F-L-M-D-Q-N-T-K (SEQ ID NO: 7);

F2: F-N-K-P-F-V-F-L-M-I-D-Q-N-T-K-V-P-L-F-M-G-K (SEQ ID NO: 1);

F3: F-N-K-P-F-V-F-L-M-I-D-Q-N-T-K (SEQ ID NO: 8);

F4: F-L-M-I-D-Q-N-T-K (SEQ ID NO: 5); and

F5: M-I-P-P-E-V-K-F-N-K-P-F-V (SEQ ID NO: 9).

As detailed below in Example 8, fragments F1, F2, F3, and F4 are all active in the SCM test, while fragment F5 is inactive. All of the active fragments contain the 9-amino-acid segment of F4, and it is reasonable that this segment might represent the active site responsible for SCM activity.

Not only are peptides F1 through F4 active in the SCM test, variants of these peptides with conservative amino acid substitutions are also expected to have SCM activity and fall within the scope of the present invention. These conservative substitutions, as outlined above, include any of isoleucine, valine, and leucine for any other of these amino acids; aspartic acid for glutamic acid and vice versa; asparagine for glutamine and vice versa; and serine for threonine and vice versa. The existence of these conservative substitutions means that the following peptides are expected to have SCM activity:

M-$X_2$-P-P-$X_5$-$X_6$-K-F-$X_9$-K-P-F-$X_{13}$-F-$X_{15}$-M-$X_{17}$-$X_{18}$-$X_{19}$-$X_{20}$-$X_{21}$-K;

F-$X_9$-K-P-F-$X_{13}$-F-$X_{15}$-M-$X_{17}$-$X_{18}$-$X_{19}$-$X_{20}$-$X_{21}$-K-$X_{23}$-P-$X_{25}$-F-M-G-K;

F-$X_9$-K-P-F-$X_{13}$-F-$X_{15}$-M-$X_{17}$-$X_{18}$-$X_{19}$-$X_{20}$-$X_{21}$-K; and

F-$X_{15}$-M-$X_{17}$-$X_{18}$-$X_{19}$-$X_{20}$-$X_{21}$-K.

In these sequences, the subscripts designating particular amino acid residues have the same meaning as stated above in the discussion of conservative amino acid substitutions in the entire 29-amino-acid synthetic SCM factor.

2. Use of the Amphipathicity Profile to Determine SCM Activity

An amphipathicity profile is a plot of the relative hydrophilicity or hydrophobicity of segments of a peptide or protein. Amino acid residues range from quite hydrophilic (e.g., charged residues or serine) to quite hydrophobic (e.g., phenylalanine). Typically, the plot is presented as a moving average over a short stretch of amino acids within the protein or peptide. For specificity and recognition purposes, amphipathicity properties of short peptides can be as significant as the amino acid sequence itself. The amphipathicity profile of the SCM-active F4 peptide fragment is strikingly similar to the amphipathicity profile of the synthetic 8-amino-acid peptide with SCM-factor activity having the sequence of F-W-G-A-E-G-Q-R (SEQ ID NO: 10), even though there is only a limited sequence homology between this peptide and the F4 peptide. By contrast, the experimental allergic encephalitogenic peptide (EAE peptide) has a sequence of F-S-W-G-A-E-G-Q-R (SEQ ID NO: 11). The presence of the relatively hydrophilic serine between the hydrophobic residues phenylalanine and tryptophan alters the amphipathicity profile considerably. As detailed in our prior U.S. patent application Ser. No. 07/167,007, the EAE peptide has no SCM factor activity.

Given the importance of the amphipathicity profile of a peptide in determining whether the peptide has SCM factor activity, a peptide of at least 9 amino acid residues including a core sequence of 9 amino acid residues having an amphipathicity profile substantially equivalent to that of the sequence F-L-M-I-D-Q-N-T-K (SEQ ID NO: 5) is expected to have SCM factor activity.

III. USE OF THE PURIFIED AND SYNTHETIC SCM FACTORS

Both the purified and synthetic SCM factors can be used as challenging agents in the SCM test, can be used to prepare antisera for the detection of the SCM factor, and can be used for the generation of DNA sequences that carry equivalent genetic information for use in a variety of genetic engineering procedures. As discussed below, this SCM factor can also be used in the management of cancer.

A. Performance of the SCM Test

The activity of both the purified SCM factor and the synthetic SCM factor, as well as the fragments of the SCM factor, is confirmed by its effect on viable SCM-responding lymphocytes in accordance with the prior publication by L. Cercek and B. Cercek, "Application of the Phenomenon of Changes in the Structuredness of Cytoplasmic Matrix (SCM) in the Diagnosis of Malignant Disorders: A Review," *Europ J. Cancer* 13, 903–915 (1977). The general cancer-associated SCM-recognition factor of the present invention produces a significant decrease in the intracellular fluorescence polarization value of potentially SCM-responding lymphocytes from donors afflicted with cancer when used to challenge such lymphocytes in the SCM test as performed as described in that article. The degree of decrease of the intracellular fluorescein fluorescence polarization value of such challenged lymphocytes is substantial—at least 20% even if ultrafiltrate from plasma from donors afflicted with cancer is used to challenge such lymphocytes, and as great as 40–55% if purified RP-HPLC fractions or synthetic peptides are used.

Two previously established procedures are important for the proper performance of the SCM test as reported herein. These procedures are the isolation of potentially SCM-responding lymphocytes and the technique of measuring the fluorescence polarization values themselves, and their conversion into numbers meaningful for the SCM test. These procedures are detailed in previous U.S. patent application Ser. No. 07/539,686 by Drs. Boris and Lea Cercek, previously incorporated by reference, and thus need not be set forth here in detail.

The result of the SCM test is a value for the intracellular fluorescein fluorescence polarization of the challenged lymphocytes. This value is designated as a P value. The higher the measured P value, the greater the degree of polarization The term "$P_s$" is used to refer to the P value of an aliquot of lymphocytes that has been challenged with a challenging agent such as an SCM factor of the present invention. Similarly, the term "$P_C$" is used to refer to the P value of an aliquot of lymphocytes not challenged with a challenging agent. When $P_S$ is compared with $P_C$, a ratio of $P_S$ to $P_C$ of less than about 0.9 is an indication of the presence of malignancy in the body of the donor of the challenged lymphocytes.

A preferred method of using the SCM factor as a challenging agent in the SCM test comprises comparing $P_S$ to the fluorescence polarization value, $P_M$ of another aliquot of the lymphocytes contacted with a mitogen such as phytohaemagglutinin (PHA), to determine an SCM response ratio, $RR_{SCM}$, where $RR_{SCM}=P_S \div P_M$. An $RR_{SCM}$ of less than about 0.9 indicates the presence of a malignancy. The use of the $RR_{SCM}$ is preferable because lymphocytes from donors free of malignancy respond to PHA but not to cancer-associated SCM factors, while lymphocytes from donors with malignancy do not respond to PHA but do respond to cancer-associated SCM factors. This double change in response pattern gives a sharper indication of the presence of a malignancy.

B. Use of the SCM Factor in the Detection of Cancer

As previously detailed in our patent application Ser. No. 07/539,686, SCM factors can be used for a number of purposes in the detection of cancer.

1. Use of SCM Factor as Challenging Agent

SCM factor, or any of its active fragments, can be used as a challenging agent in the SCM test for the detection of cancer. Lymphocytes from donors with cancer, but not from donors free of cancer, are primed to respond to cancer-associated factors in the SCM test. Accordingly, only lymphocytes from donors with cancer respond to SCM factor with a decrease in intracellular fluorescein fluorescence polarization value in the SCM test. This response constitutes an early warning that cancer cells producing SCM factor are present in the body of the lymphocyte donor, even when the number of tumor cells or the size of the tumor might not be otherwise detectable.

2. Detection of Receptors Specific for SCM Factor

SCM factor molecules or fragments that are labeled can be used to detect the presence of receptors for SCM molecules on the SCM-responding fraction of lymphocytes. The label can be, but is not limited to, a radioactive label, a fluorescent label, a chemiluminescent label, or an enzyme label. The presence of these receptors is itself an indication of cancer. They can be detected using flow cytometry, fluorescence microscopy, enzyme-linked assays, or other assays for lymphocyte receptors. If the SCM molecules are labeled with radioactive isotopes, autoradiography, scintigraphy, and other detection methods for radionuclides can be used to detect the presence of receptors for SCM factors.

If SCM-responding lymphocytes are isolated, washed, and incubated with a saturating quantity of labeled SCM factor, the extent of the binding of the SCM factor to the lymphocytes indicates the number of SCM factor receptors present per lymphocyte. This test can be used to indicate the sensitization of SCM-responding lymphocytes to the SCM factor and can be used as an alternative to the SCM test to detect the presence of cancer; it can also be used to confirm the findings of the SCM test.

3. Detection of SCM Factor Molecules in Cancer Biopsies

By flow cytometry, fluorescence microscopy, or enzyme-linked assays, SCM factor molecules can be detected in cancer biopsies using appropriately labeled anti-SCM factor antibodies. Because SCM factor molecules are produced in quantity by cancer cells, their presence in biopsy specimens is a strong confirmation of the cancerous nature of the tissues from which the biopsy specimen is taken.

4. Detection of SCM Factor Molecules in Body Fluids

As shown above, SCM factor molecules are excreted by cancer cells into body fluids such as blood plasma or urine. The presence of SCM factor in body fluids can therefore be used as a general cancer-specific marker.

IV. EFFECT OF SCM FACTORS AND FRAGMENTS ON NATURAL KILLER (NK) AND LYMPHOKINE-ACTIVATED KILLER (LAK) ACTIVITY

Unexpectedly, the synthetic SCM factor was found to depress both natural killer (NK) activity and lymphokine-activated killer (LAK) activity in peripheral blood lymphocytes. Particularly effected was NK activity in the subclass of SCM-responding lymphocytes. Because both NK and LAK activities are believed to be involved in immune defense, this result suggests that the SCM factor is involved in the failure of immune defense to suppress tumor growth in vivo.

A. Effect on NK Activity

1. Effect of Intact SCM Factor

Both the natural SCM factor as ultrafiltrate (Example 10), and the purified 29-amino-acid synthetic SCM factor (Example 11), inhibit NK activity of SCM-responding lymphocytes when incubated with isolated SCM-responding lymphocytes. The SCM factors also depress the NK activity of peripheral blood lymphocytes (PBL).

When SCM-responding lymphocytes and PBL were incubated with 35 femtomoles of the 29-amino-acid synthetic SCM factor, the percentage cytotoxicity of both SCM-responding lymphocytes and PBL was suppressed by 97% to 99.9%. The suppression was not reversed by washing the treated lymphocytes three times before the cytotoxicity assay (Example 11). The results shown in FIG. 1 (Example 11) show that under identical experimental conditions, the percentage of cytotoxicity decreased with decreasing effector cell/target cell ratios. However, when lymphocytes were treated with 35 femtomoles of the synthetic SCM factor peptides per cell, the cytotoxicity was suppressed to the same level regardless of the effector cell/target cell ratios. The degree of suppression also did not depend on the molarity of the synthetic SCM-factor peptide solution, which varied between 70 μmole/l and 7 μmole/l. The dose response data (FIG. 2) show that for a 50% decrease of cytotoxicity, only 12 femtomoles of the synthetic SCM peptide per lymphocyte was required.

There is a dose-time relationship with respect to the effect of the synthetic SCM peptide on the suppression of NK activity. Incubation of PBL with only 3.5 femtomoles of synthetic SCM peptide per lymphocyte for 3 hours had only a minimal effect on the NK activity of the lymphocytes. However, after 23 hours of incubation with 3.5 femtomoles of peptide per lymphocyte, the cytotoxicity decreased to only 60% of the control value. The long incubation time affected neither the NK activity of the untreated cells nor the viability of the cells (Example 11).

The synthetic SCM factor did not affect the binding of NK lymphocytes to target cells (Example 14). However, incubation of lymphocytes with 35 femtomoles of the synthetic SCM factor for 3 hours decreased the release of interleukin-2 (IL-2) by 30% and the release of tissue necrosis factor α (TNFα) by 78.6% after an 18-hour incubation of lymphocytes with NK-susceptible cancer cells at an effector-target ratio of 1:1 (Example 15). Washing of the lymphocytes that had been incubated with synthetic SCM factor did not restore the cytotoxic effectiveness (Example 11; Table 3).

Because IL-2 is known to enhance the NK activity of lymphocytes, an attempt was made to restore the cytotoxicity of SCM factor-treated lymphocytes by a subsequent incubation with IL-2. A three-hour incubation with IL-2 did not restore the cytotoxicity of the lymphocytes (Example 16; Table 8).

Because both the natural isolated SCM factors and the synthetic 29-amino-acid SCM factor depressed NK activity, Applicants believe that it is a property shared by the SCM factors described above, including, but not limited to, the natural isolated SCM factors of 29 and 35 amino acids, and peptides related thereto by one or more conservative amino acid substitutions as described above.

2. Effect of SCM Factor Fragments

In addition to the intact SCM factors, certain fragments of SCM factor also depress NK activity (Example 12). These peptides includes the fragment F2 (residues 8–29). None of the other fragments tested, including F1 (residues 1–22), F3 (residues 8–22), F4 (residues 14–22), F5 (residues 1–13), F7 (residues 14–29), and F8 (residues 23–29) showed any depression of NK activity under the same conditions. The failure of fragment F7 (residues 14–29) to depress NK activity indicates that residues 8–14 are involved in the depression of NK activity. Similarly, the failure of fragment F3 (residues 8–22) to depress NK activity indicates that residues 23–29 are also involved.

Fragment F2 (residues 8–29), on an equimolar basis, is as effective a suppressor of NK activity as is the entire 29-amino-acid synthetic SCM molecule.

These results indicate that the SCM-factor molecule is multifunctional, and that these various functions are located in discrete domains of the molecule. As described in prior U.S. patent application Ser. No. 07/539,686, residues 14–22 comprise the domain responsible for causing a decrease in the structuredness of the cytoplasmic matrix of lymphocytes isolated from cancer patients.

Residues 8–29 comprise the domain responsible for suppressing immune defense, as disclosed above. Both residues 8–14 and residues 23–29 are required for this activity.

Residues 1–7 have been determined to be responsible for the protease protection activity of the SCM factor, as disclosed in application Ser. No. 07/539,686. A tryptic fragment containing only these residues (M-I-P-P-E-V-K (SEQ ID NO: 12)) was as effective in protecting serine proteases from the effects of $\alpha_1$-PI as was the entire 29-amino-acid synthetic SCM-factor molecule.

Additionally, the three methionine residues of the SCM-factor molecule, located at residues 1, 16, and 27, are believed to scavenge activated oxygen species such as superoxide, hydroxyl radical, and hydrogen peroxide, generated by leukocytes and believed to be involved in the killing of tumor cells by phagocytosis (B. D. Davis et al., "Microbiology" (4th ed., J. B. Lippincott, Philadelphia, 1990), pp. 499–500).

B. Effect on Lymphokine-Activated Killer (LAK) Activity

Unexpectedly, the SCM factor peptides also have the property of inhibiting the LAK activity of peripheral blood lymphocytes when the lymphocytes are incubated with the peptide.

When NK-resistant, LAK-sensitive Daudi Burkitt lymphoma cells were used as target cells and peripheral blood lymphocytes were used as effector cells, the control cytotoxicity in a 4-hour assay at an effector cell/target cell ratio of 40:1 was only 13.5% (Example 12). After incubation of PBL with recombinant interleukin-2 (rIL-2) (1,000 units/2× $10^6$ cells) for 18 hours, the killing efficiency of the cells was augmented, with the cytotoxicity against Daudi cells increasing to 77.5% (574% of the control cytotoxicity). Incubation of these stimulated LAK cells for three hours with 35 femtomoles of synthetic SCM factor per cell decreased the rIL-2 stimulated LAK toxicity against Daudi cells to only 3.4%, or only 25.2% of the original control NK cytotoxicity.

This result may explain the disappointing results thus far obtained for treatment of cancer with lymphokines (Mesler et al., "Large Scale Production of Human Lymphokine Activated Killer Cells for Use in Adoptive Immuno Therapy," *J. Immunol. Meth.* 88:265–275 (1986); T. L. Whiteside, "Human Tumor-Infiltrating Lymphocytes and Their Characterization," in Interleukin-2 and Killer Cells in Cancer, Ch. 10, pp. 133–151; B. W. Hancock & R. C. Rees, "Interleukin-2 and Cancer Therapy," *Cancer Cells* 2:29–32 (1990)). These results suggest that the SCM factors present in the cancer cells and the blood plasma of cancer patients block the effect of the lymphokines and prevent the lymphokines from stimulating LAK activity. As detailed below, the use of an agent capable of blocking the immune defense suppressive activities of an SCM-factor peptide can block suppression of the NK and LAK activities and provide a new way of treating cancer (Section VI).

V. IMMUNOCHEMISTRY OF THE NATURAL AND SYNTHETIC SCM FACTOR MOLECULES AND FRAGMENTS

Among the agents useful for blocking or reversing the immune defense suppressive activities of SCM-factor peptides are antibodies to both intact SCM factor molecules and fragments.

A. Preparation of Antibodies

1. Antibodies to Intact SCM Factor Molecules

Methods for antibody preparation suitable for intact SCM factor molecules are well known in the art. Such methods are described for example in E. Harlow and D. Lane, "Antibodies: A Laboratory Manual," Cold Spring Harbor Laboratory, 1988, incorporated herein by this reference. Intact SCM factors of 29–35 amino acid residues, both natural and synthetic, are sufficiently large to be immunogenic when injected into antibody-forming animals. Preferably, the injection is with Freund's adjuvant, most preferably with complete Freund's adjuvant. Alternatively, the intact 29–35 amino acid natural and synthetic SCM factors can be coupled to a carrier protein for antibody production, as described below. Suitable carrier proteins and conjugation methods are well known in the art. Suitable carrier proteins include, but are not limited to, keyhole limpet hemocyanin, bovine serum albumin, ovalbumin, polylysine, and purified protein derivative of tuberculin (PPD).

A large number of coupling agents are also well known in the art, including, but not limited to, bis (sulfosuccinimidyl) suberate, dimethyl adipimate, dimethyl pimelimidate, dimethyl suberimidate, disuccinimidyl suberate, glutaraldehyde, m-maleimidobenzyl-N-hydroxysuccinimide, sulfo-m-maleimidobenzyl-N-hydroxysuccinimide, sulfosuccinimidyl 4-(N-maleimidomethyl)-cyclohexane-1-carboxylate, sulfosuccinimidyl 4-(p-maleimidophenyl) butyrate, and N-succinimidyl bromoacetate. For heterobifunctional cross-linkers in which one of the functionalities reacts with the sulfhydryl group, such as N-succinimidyl bromoacetate, the peptide to be coupled can be extended at its carboxyl terminus by an additional cysteine residue for coupling (N. S. Bernatowicz and G. R. Matsueda, "Preparation of Peptide-Protein Immunogens Using N-Succinimidyl Bromoacetate as a Heterobifunctional Cross-Linking Agent," *Anal Biochem.* 155:95–102 (1986)). Among the animals that can be used for antibody production are rabbits, goats, horses, and sheep. For many applications, the use of goats for immunization is suitable. However, as discussed below, for in vivo treatment of human cancer, autologous human antibodies are strongly preferred.

Monoclonal antibodies can be prepared according to methods well known in the art (Harlow and Lane, supra). These methods result in the generation of immortal hybridoma cells producing monoclonal antibodies of the desired specificity.

Monoclonal antibodies useful in the processes and compositions of the present invention can be mouse, rat, human, or hybrid, depending on the animal immunized and the myeloma used as fusion partner, as disclosed in J. W. Goding, "Monoclonal Antibodies: Principles and Practice," (2d ed. Academic Press, London, 1986), incorporated herein by this reference. However, the use of human monoclonal antibodies is strongly preferred, as the use of hybrid or non-human monoclonal antibodies can induce an undesirable immune response. Alternatives to the use of human monoclonal antibodies include: (1) chimeric mouse-human monoclonal antibodies containing mouse variable regions and human constant regions; and (2) monoclonal antibodies generated by grafting the complementarity-determining regions (CDRs) from mouse antibodies into human immunoglobulin genes, based on sequence information and modeling of the antigen-reactive surface. These alternatives are described in E. S. Golub & D. R. Green, "Immunology: A Synthesis" (2d ed , 1991, Sinauer Associates, Sunderland, Mass.), pp. 143–147, incorporated herein by this reference.

2. Antibodies to SCM-Factor Peptide Fragments

Antibodies can also be produced to SCM-factor fragments, as described below. The use of antibodies to SCM-factor fragments is generally preferable for blocking suppression of immune defense, as it may reduce the possibility of cross-reactions. Antibodies are preferably produced to a SCM-factor peptide fragment by extending the fragment at its carboxyl-terminus with an additional cysteine residue (Bernatowicz & Matsueda, Supra), and then coupling the extended fragment to a carrier protein as described above.

Antibodies to SCM factor can be formed by immunizing an antibody-forming mammal with at least one conjugate selected from the group consisting of:

(1) a peptide selected from the group consisting of a peptide of the sequence F-L-M-I-D-Q-N-T-K-V-P-L-F-M-G-K-C (SEQ ID NO: 3) and peptides related thereto by one or more conservative amino acid substitutions conjugated at its carboxy-terminal cysteine residue to a carrier protein;

(2) a peptide selected from the group consisting of a peptide of the sequence F-N-K-P-F-V-F-L-M-I-D-Q-N-T-K-V-P-L-F-M-G-K-C (SEQ ID NO: 4) and peptides related thereto by one or more conservative amino acid substitutions conjugated at its carboxy-terminal cysteine residue to a carrier protein; and (3) a macromolecular aggregate composed of multiple copies of peptides selected from the group consisting of:

(a) a peptide selected from the group consisting of a peptide of the sequence F-L-M-I-D-Q-N-T-K-V-P-L-F-M-G-K-C (SEQ ID NO: 3) and peptides related thereto by one or more conservative amino acid substitutions;

(b) a peptide selected from the group consisting of a peptide of the sequence F-N-K-P-F-V-F-L-M-I-D-Q-N-T-K-V-P-L-F-M-G-K-C (SEQ ID NO: 4) and peptides related thereto by one or more conservative amino acid substitutions;

(c) a peptide selected from the group consisting of a peptide of the sequence F-N-K-P-F-V-F-L-M-I-D-Q-N-T-K-V-P-L-F-M-G-K (SEQ ID NO: 1) and peptides related thereto by one or more conservative amino acid substitutions; and (d) a peptide selected from the group consisting of a peptide of the sequence F-L-M-I-D-Q-N-T-K-V-P-L-F-M-G-K (SEQ ID NO: 2) and peptides related thereto by one or more conservative amino acid substitutions.

B. Particular Antibodies Useful for Blocking Suppression of Immune Defense by SCM-Factor Peptides Among particular antibodies useful for blocking suppression of immune defense by SCM-factor peptides are the following:

(1) Antibodies produced by immunization of an antibody-producing animal with the peptide M-I-P-P-E-V-K-F-N-K-P-F-V-F-L-M-I-D-Q-N-T-K-V-P-L-F-M-G-K-C (SEQ ID NO: 13) conjugated at its carboxy-terminal cysteine residue to a carrier protein;

(2) Antibodies produced by immunization of an antibody-producing animal with the peptide M-I-P-P-E-V-K-F-N-K-P-F-V-F-L-M-I-D-Q-N-T-K-V-P-L-F-M-G-K (SEQ ID NO: 6);

(3) Antibodies produced by immunization of an antibody-producing animal with the peptide F-L-M-I-D-Q-N-T-K-V-P-L-F-M-G-K-C (SEQ ID NO: 3) conjugated at its carboxy-terminal cysteine residue to a carrier protein; and (4) Antibodies produced by immunization of an antibody-producing animal with the peptide F-N-K-P-F-V-F-L-M-I-D-Q-N-T-K-V-P-L-F-M-G-K-C (SEQ ID NO: 4) conjugated at its carboxy-terminal cysteine residue to a carrier protein.

Preferably, antibodies of categories (1) and (3) are used for in vivo therapy, as these antibodies are less likely to impair the normal functions of $\alpha_1$-antitrypsin by cross-reaction with that protein.

C. Use of Antibody Fragments and Hybrid Antibodies

Because the formation of an antigen antibody lattice is not necessary to block suppression of immune defense by SCM-factor peptides in many applications, the use of monovalent or divalent antibody fragments produced from antibodies of the appropriate specificity, either polyclonal or monoclonal. The fragments can be Fab, Fab', or F(ab')$_2$.

Additionally within the scope of the invention are antibodies of hybrid specificity produced by in vitro reassociation of antibody subunits.

D. Specificity of Antibodies Useful in Blocking Suppression of Immune Defense by SCM-Factor Peptides Among antibodies useful in blocking the suppression of immune defense are antibodies that bind particular domains of the synthetic SCM-factor peptide with sequences given above.

The domain bound must be distinguished from the peptide or fragment used for immunization. In some cases, a domain can be bound with sufficient specificity even though the peptides or fragment used for immunization includes only a portion of that domain. In other cases, regions outside of the domain can be included in the peptide or fragment used for immunization without adversely affecting the specific binding of the antibodies to its domain. In particular, the terminal cysteine residue added for immunization does not affect the specificity of the antibodies generated thereby.

One antibody that is useful for blocking suppression of immune defense activity specifically binds a domain selected from the group consisting of F-N-K-P-F-V-F-L-M-I-D-Q-N-T-K-V-P-L-S-M-G-K (SEQ ID NO: 1) and a domain related thereto by one or more conservative amino acid substitutions. Preferably, the domain specifically bound has the sequence F-$X_9$-K-P-F-$X_{13}$-F-$X_{15}$-M-$X_{17}$-$X_{18}$-$X_{19}$-$X_{20}$-$X_{21}$K-$X_{23}$-P-$X_{25}$-F-M-G-K, wherein $X_9$, $X_{19}$, and $X_{20}$ are each independently selected from the group consisting of Q and N; $X_{13}$, $X_{15}$, $X_{17}$, $X_{23}$, and $X_{25}$ are each independently selected from the group consisting of I, L, and V; $X_{18}$ is selected from the group consisting of D and E; and $X_{21}$ is selected from the group consisting of S and T. Most preferably, this domain has the sequence F-N-K-P-F-V-F-L-M-I-D-Q-N-T-K-V-P-L-F-M-G-K (SEQ ID NO: 1), corresponding to amino acid residues 8–29 of the synthetic SCM factor peptide.

Another antibody useful for blocking suppression of immune defense activity specifically binds a domain selected from the group consisting of F-L-M-I-D-Q-N-T-K-V-P-L-F-M-G-K (SEQ ID NO: 2) and a domain related thereto by one or more conservative amino acid substitutions. Preferably, this domain has the sequence F-$X_{15}$-M-$X_{17}$-$X_{18}$-$X_{19}$-$X_{20}$$X_{21}$-K-$X_{23}$-P-$X_{25}$-F-M-G-K, wherein $X_{15}$, $X_{17}$, $X_{23}$, and $X_{25}$ are each independently selected from the group consisting of I, L, and V; $X_{18}$ is selected from the group consisting of D and E; and $X_{19}$ and $X_{20}$ are each independently selected from the group consisting of S and T. Most preferably, this domain has the sequence F-L-M-I-D-Q-N-T-K-V-P-L-F-M-G-K (SEQ ID NO: 2), residues 14–29 of synthetic SCM factor.

VI. METHODS FOR BLOCKING SUPPRESSION OF IMMUNE DEFENSE CAUSED BY SCM FACTORS

We have discovered that a number of agents are capable of blocking the immune defense suppressive activities of SCM-factor peptides, and thus blocking suppression of immune defense caused by SCM factors in cancer patients. These agents include:

(1) antibodies;

(2) a high-molecular weight factor found in blood plasma;

(3) antisense peptides; and (4) direct or indirect inhibitors of protein synthesis in tumor cells.

A method for blocking suppression of at least one of the NK and LAK immune defense mechanisms in a cancer patient comprises administering to a cancer patient an agent capable of blocking the immune defense suppressive activities of the SCM-factor peptide in a quantity sufficient to block suppression at least one of the natural killer (NK) and lymphocyte activated killer (LAK) immune defense mechanisms. The blocking of the suppression of immune defense mechanisms occurs by scavenging, inactivation, and elimination of the circulating SCM factor as the result of the specific binding of the agent to the SCM factor.

Typically, the blocking of suppression of immune defense comprises a stimulation of synthesis and/or release of at least one humoral factor selected from the group consisting of interleukin-2 (IL-2) and tissue necrosis factor $\alpha$ (TNF$\alpha$). The method can then further comprise determining the degree of blocking of suppression of surveillance by monitoring an increase in synthesis and/or release of the at least one humoral factor.

The agent capable of blocking the immune defense suppressive effect of SCM-factor peptide is preferably injected by a conventional injection route, such as intravenously, intramuscularly, or subcutaneously.

This therapy method can be combined with the administration of at least one humoral factor capable of stimulating at least one of the NK and LAK activities. Such humoral factors include, but are not limited to, IL-2 and TNF$\alpha$. These humoral factors would be administered according to generally-recognized dosages and routes of administration. The most effective route of administration and dosage of regimen will depend on the severity and course of the malignant disease, the patient's health and response to treatment, and the judgment of the treating health professional.

This therapy method can also be combined with administration of agents that inhibit the synthesis of SCM-factor peptides in tumor cells, such as by the inhibition of protein synthesis. The inhibitor of protein synthesis can be an agent that directly suppresses protein synthesis, such as cycloheximide or actinomycin D, or an agent that suppresses metabolic activity in tumor cells, such as ascorbic acid. A preferred inhibitor is ascorbic acid, which is substantially non-toxic and can be administered orally or by injection.

A. Administration of Antibodies

The antibodies disclosed in Section V above are suitable agents for administration to a cancer patient in order to block suppression of immune defense by SCM factor. Both antibodies to the complete 29-amino-acid synthetic SCM factor and antibodies to fragments thereof can be used. One particularly useful antibody is an antibody produced by immunization with the fragment of the synthetic SCM factor encompassing residues 14–29 linked to a carrier protein through an additional cysteine residue at the carboxyl-terminus of the fragment. This antibody is less likely to cross-react with analogous sequences in the protease inhibitor $\alpha_1$-PI then are antibodies prepared by to the intact synthetic SCM factor molecule.

The quantity of antibody used is preferably sufficient to react with substantially all the SCM factor present in the blood plasma, and therefore depends on the quantity of SCM factor present in the plasma of the patient being treated. Although applicants do not intend to be bound rigorously by the following calculation, it provides some guidance as to the quantity of antibody required. The level of SCM factor in ultrafiltrates of plasma of cancer patients ranges from about 5 ng/ml up to about 25 ng/ml. For a normal blood volume of about 4.50 liters, this concentration results in a total quantity of SCM-factor peptide of about 11 to 56 µg in the plasma when the ratio of plasma volume to total blood volume (about 0.5) is taken into account. Although each intact antibody can bind two SCM factor molecules, it is desirable to allow for binding only one SCM factor molecule per antibody. To ensure that substantially all SCM molecules are bound, at least a twofold excess of antibody molecules over SCM factor molecules is preferably used. This means that the optimum dose of immunoglobulin is about 1 to 5 mg of immunoglobulin protein as IgG. This calculation merely establishes an estimate for the minimum quantity of antibody; more antibody can be used if desired.

If monovalent Fab fragments, of molecular weight of about 50,000, are used, the minimum quantity of antibody fragments to be administered is about 0.33 mg. In some applications, the use of monovalent antibody fragments is preferred to the use of intact antibodies, if the formation of large SCM factor-antibody complexes is considered undesirable. The presence of such large antigen-antibody complexes in the peripheral blood can possibly cause serum sickness or other allergic reactions.

Preferably, the antibody administered are autologous for the patient. Such autologous antibodies can be produced, for example, by culturing in vitro of autologous B lymphocytes producing antibodies capable of blocking the immune defense suppressive activities of the SCM-factor peptide, as described in J. Banchereau & F. Rousset, "Growing Human B Lymphocytes in the CD40 System," *Nature* 353:678–679 (1991). Less preferably, especially for short-term therapy or in emergencies, non-autologous compatible human antibodies can be administered.

B. Administration of High-Molecular-Weight Blood Plasma Factor

Alternatively, a high-molecular-weight factor from blood plasma can be administered. This factor has the property of reversing suppression of the immune defense functions. The factor is present in autologous, cell-free blood plasma and is substantially removed by ultrafiltration through a filter with a nominal molecular weight cutoff of 50 kD.

The reversal of suppression decreased to only 30% after incubation of the NK suppressed cells with ultrafiltrates with nominal molecular weight cutoffs of 100 kD and was almost completely abolished on incubation with ultrafiltrates with nominal molecular weight cutoffs of 50 kD.

C. Administration of Antisense Peptides

As an alternative to the use of antibodies, antisense peptides encoded by the antisense strand of the DNA whose sense strand encodes for SCM factor can also be used to inhibit the activity of SCM factor and block the suppression of immune defense by it. As reported in Y. Shai et al., "Antisense Peptide Recognition of Sense Peptides: Sequence Simplification and Evaluation of Forces Underlying the Interaction," *Biochemistry* 28:8804–8811 (1989), and G. Fassina et al., "Recognition Properties of Antisense Peptide to Arg$^8$-Vasopressin/Bovine Neurophysin II Biosynthetic Precursor Sequences," *Biochemistry* 28:8811–8818 (1989), peptides that are encoded by the antisense strand of a DNA molecule whose sense strand encodes a physiologically active peptide often interact specifically with that peptide. The "sense strand" is the strand of the DNA identical in sequence with the messenger RNA corresponding to it (except for the substitution of U in mRNA for T in DNA), while the "antisense strand" is complementary to the sequence of the mRNA. For example, if the sense strand has the sequence 5'-ATG-3', the antisense strand has the sequence 5'-CAT-3'.

As applied to the blockage of the immune defense suppressing effects of SCM factor, the antisense peptide has an amino acid sequence encoded by the antisense strand of a DNA sequence whose sense strand encodes a domain of the SCM factor. The domain encoded by the sense strand has a sequence such that antibodies capable of binding specifically to the domain block the immune defense suppressive effect of SCM factor.

These antisense peptides include, but are not limited to:

(1) A peptide encoded by the antisense strand of the DNA sequence whose sense strand encodes a peptide with the sequence F-$X_9$-K-P-F-$X_{13}$-F-$X_{15}$-M-$X_{17}$-$X_{18}$-$X_{19}$-$X_{20}$-$X_{21}$-K-$X_{25}$-F-M-G-K, where the subscripts are defined as described above;

(2) A peptide encoded by the antisense strand of the DNA sequence whose sense strand encodes the sequence F-N-K-P-F-V-F-L-M-I-D-Q-N-T-K-V-P-L-F-M-G-K (SEQ ID NO: 1);

(3) A peptide encoded by the antisense strand of a DNA sequence whose sense strand encodes a peptide with the sequence F-$X_{15}$-M-$X_{17}$-$X_{18}$-$X_{19}$-$X_{20}$-$X_{21}$-K-$X_{23}$-P-$X_{25}$-F-M-G-K; and (4) A peptide encoded by the antisense strand of the DNA sequence whose sense strand encodes the sequence F-L-M-I-D-Q-N-T-K-V-P-L-F-M-G-K (SEQ ID NO: 2).

The antisense peptides are typically used under the same conditions of concentration in vivo as the antibodies, except that, because the antisense peptides are smaller, typically from about 1,800–3,300 molecular weight, the required concentration, expressed in mass per volume, is proportionately smaller than that for the antibodies. The molar concentrations, however, are equivalent.

VII. IMMUNIZATION WITH SCM-FACTOR PEPTIDES

An alternative treatment method according to the present invention is a method of inducing production in a mammal of antibodies capable of binding an SCM-factor peptide by immunization of the mammal. Such antibodies scavenge, inactivate, and eliminate the circulating SCM factors before the SCM factors can suppress the NK or LAK activities of the lymphocytes.

Immunization with SCM factors or conjugates of SCM factors with a carrier protein was not toxic to the immunized animals (Example 9). No side effects were seen in immunized animals.

As shown below in Example 20, anti-SCM factor antibody is present in both cancer patients and individuals free of cancer. The level of antibody is markedly greater in cancer patients, which suggests that the production of anti-SCM factor antibody represents a response to the presence of higher levels of SCM factor in cancer patients, although insufficient to suppress the immune defense-inhibiting effects of SCM factor. Thus, immunization with SCM factor in a form that is effective for eliciting antibody production may serve to raise the level of antibody to SCM factor and provide a prophylactic against malignancies, as well as aiding in immunotherapy of cancer. Immunization may be particularly desirable in patients with a family history of cancer or in patients who have had a malignant tumor removed surgically or suppressed by radiation therapy or chemotherapy, but are at risk of recurrence of the cancer.

Preferably, the method comprises immunizing the mammal with at least one conjugate selected from the group consisting of:

(1) a peptide selected from the group consisting of a peptide of the sequence F-L-M-I-D-Q-N-T-K-V-P-L-F-M-G-K-C (SEQ ID NO: 3) and peptides related thereto by one or more conservative amino acid substitutions conjugated at its carboxy-terminal cysteine residue to a carrier protein;

(2) a peptide selected from the group consisting of a peptide of the sequence F-N-K-P-F-V-F-L-M-I-D-Q-N-T-K-V-P-L-F-M-G-K-C (SEQ ID NO: 4) and peptides related thereto by one or more conservative amino acid substitutions conjugated at its carboxy-terminal cysteine residue to a carrier protein; and (3) a macromolecular aggregate composed of multiple copies of peptides selected from the group consisting of:
  (a) a peptide selected from the group consisting of a peptide of the sequence F-L-M-I-D-Q-N-T-K-V-P-L-F-M-G-K-C (SEQ ID NO: 3) and peptides related thereto by one or more conservative amino acid substitutions;
  (b) a peptide selected from the group consisting of a peptide of the sequence F-N-K-P-F-V-F-L-M-I-D-Q-N-T-K-V-P-L-F-M-G-K-C (SEQ ID NO: 4) and peptides related thereto by one or more conservative amino acid substitutions;
  (c) a peptide selected from the group consisting of a peptide of the sequence F-N-K-P-F-V-F-L-M-I-D-Q-N-T-K-V-P-L-F-M-G-K (SEQ ID NO: 1) and peptides related thereto by one or more conservative amino acid substitutions; and
  (d) a peptide selected from the group consisting of a peptide of the sequence F-L-M-I-D-Q-N-T-K-V-P-L-F-M-G-K (SEQ ID NO: 2) and peptides related thereto by one or more conservative amino acid substitutions.

The macromolecular aggregate of (3) is formed without conjugation to a carrier protein. The macromolecular aggregate is formed by linkage of the carboxy-terminal residues of each of the peptides to a branching lysine core. A suitable lysine core has eight branches, although lysine cores having 16 or 32 branches can also be used, with each branch carrying one of the peptides recited above. Preferably, each branch of the lysine core carries the same peptide, although it is also possible to use lysine cores in which the branches carry two or more different peptides. The use of branching lysine cores to form molecular aggregates for immunization is described in D N Posnett et al ,. "A Novel Method for Producing Anti-Peptide Antibodies," *J. Biol. Chem.* 283:1719–1725 (1988), incorporated herein by this reference.

Most preferably, the conjugate used for immunization comprises the peptide F-L-M-I-D-Q-N-T-K-V-P-L-F-M-G-K-C (SEQ ID NO: 3) conjugated at its carboxy-terminal cysteine residue to a carrier protein. Less preferably, the conjugate used for immunization comprises the peptide F-N-K-P-F-V-F-L-M-I-D-Q-N-T-K-V-P-L-F-M-G-K-C (SEQ ID NO: 4) conjugated at its carboxy-terminal cysteine residue to a carrier protein.

Immunization of human subjects with these conjugates produces antibodies that scavenge SCM-factor peptides in the body fluids of the immunized subject to support immunotherapy or aid in cancer prevention.

VIII. PHARMACEUTICAL COMPOSITIONS

The invention further comprises pharmaceutical compositions useful in blocking the in vivo immune defense suppressive effects of SCM factor.

In general, a pharmaceutical composition according to the present invention comprises:

(1) an agent capable of blocking the immune defense suppressive effect of a SCM-factor peptide in a quantity sufficient to block suppression of immune defense in a patient with cancer; and (2) a pharmaceutically acceptable carrier.

The agent capable of blocking the immune defense suppressive effect can be an antibody, antibody fragment, antisense peptide, or high-molecular-weight blood plasma factor, as described above. The agent can alternatively be an agent that suppresses synthesis of SCM-factor peptides in cancer cells. Such an agent can either directly suppress protein synthesis in cancer cells, such as cycloheximide or actinomycin D, or suppress protein synthesis via suppression of the metabolic activity in cancer cells, such as ascorbic acid.

Conventional pharmaceutically acceptable carriers known in the art can include alcohols, e.g., ethyl alcohol, serum proteins, human serum albumin, liposomes, buffers such as phosphates, water, sterile saline or other salts, electrolytes, glycerol, hydroxymethylcelluose, propylene glycol, polyethylene glycol, polyoxyethylenesorbitan, other surface active agents, vegetable oils, and conventional antibacterial or anti-fungal agents, such as parabens, chlorobutanol, phenol, sorbic acid, thimerosal, and the like. A pharmaceutically-acceptable carrier within the scope of the present invention meets industry standards for sterility, isotonicity, stability, and non-pyrogenicity. The particular carrier used depends on the concentration of the agent capable of blocking the immune defense suppressive effect and the intended route of administration.

IX. TREATMENT KITS

The invention further comprises kits for stimulating immune response of a cancer patient. The kit comprises, in separate containers:

(1) a pharmaceutical composition as described in Section VIII; and (2) a composition comprising:
  (a) a lymphokine capable of stimulating at least one of the natural killer (NK) and lymphokine activated killer (LAK) immune defense mechanisms in a quantity sufficient to stimulate immune defense; and
  (b) a pharmaceutically acceptable carrier.

The kit can optionally further comprise, in a separate container:

(3) an inhibitor of protein synthesis with specific effects on tumor cells, optionally with a pharmaceutically acceptable carrier.

The lymphokine can be interleukin-2 (IL-2), tissue necrosis factor α (TNFα) or interferon. Preferably, the lymphokine is interleukin-2 or tissue necrosis factor α.

The quantity of the lymphokine used in the kit depends on the size, age, and clinical state of the patient. Dosages for these lymphokines are well known in the art. For IL-2, a typical dose is 1,000 units/ml blood plasma.

The inhibitor of protein synthesis can be an agent that directly suppresses protein synthesis, such as cycloheximide or actinomycin D, or an agent that suppresses metabolic activity in tumor cells, such as ascorbic acid. A preferred inhibitor is ascorbic acid, which is substantially non-toxic and can be administered orally or by injection. It can be used in doses of up to at least about 20 g/day for humans. Although ascorbic acid requires no carrier, one may be desirable for greater tolerability. Cycloheximide or actinomycin D are preferably administered with a suitable pharmaceutically acceptable carrier.

EXAMPLES

The following Examples illustrate: (1) the isolation, purification, characterization, and activities of substantially purified SCM factor from body fluids of patients with cancer; (2)

the characterization and activities of synthetic SCM factor and peptides comprising partial sequences of synthetic SCM factor; (3) the effect of natural and synthetic SCM factor, as well as fragments of synthetic SCM factor, in suppressing natural killer (NK) and lymphokine-activated killer (LAK) activity; and (4) the use of antibodies to synthetic SCM factor to block the suppression of NK and LAK activity. These Examples are for illustrative purposes only and are not to be construed as limiting the invention.

Example 1

Initial Purification of the General Cancer-Associated SCM Factor from Blood Plasma Blood samples from patients positively diagnosed as having active cancer, such as cancer of the breast, lung, colon, ovary, cervix, uterus, larynx, or skin (basal cell carcinoma and malignant melanoma) were collected into heparinized vials such as Vacutainer™ tubes. Twenty-milliliter portions of the blood samples were centrifuged at about 1200×g for approximately 40 min. The plasma above the sedimented blood cells was collected and filtered by pressure through a porous membrane filter such as an Amicon™ UM2 or YM2 filter, with a 1000-dalton molecular weight cutoff. These ultrafiltrates were lyophilized or stored at 4° C. until further purification. When these ultrafiltrates were used in the SCM test procedure described above, in every case, the ultrafiltrate caused the SCM-responding lymphocytes to respond characteristically with a decrease in P value, as they would have if they had been contacted with the cancerous tissue itself or with extracts of cancerous tissue.

Example 2

Further Purification of the SCM Factor of Example 1

The lyophilized powder from the samples of Example 1 was dissolved in 2 ml of sterile preservative-free water for injections. At this stage, the SCM activity of the preparations was ascertained, and active samples from donors with the same type and site of cancer were pooled. The pooled samples were desalted on an 0.9×18 cm column of Sephadex™ G-10, which has a fractionation range of from 0 to 700 daltons. The sample volume per column chromatographic run did not exceed 25% of the column volume. Elution was carried out with double distilled water at the linear elution speed of 8 to 9 cm/hr. The desalting was carried out at room temperature (21°–23° C.). One-ml fractions eluting at between 0.3 and 0.5 times the total chromatographic bed volume were collected and the optical densities of the fractions determined. The SCM activity was contained within the first elution peak. The presence of SCM activity in that peak was confirmed by an SCM test. An aliquot of the first elution peak, prepared from an ultrafiltrate originally derived from plasma of a patient with breast cancer reduced the P value of lymphocytes from a patient with breast cancer to 86.3% of the control value in the SCM test, indicating the presence of SCM activity. These fractions were collected and lyophilized.

The eluate was further purified by fractionation on a Sephadex™ G-50 gel filtration column, which has a fractionation range of from 1500 to 30,000 daltons. The lyophilized desalted samples were dissolved in 50 mM $NH_4HCO_3$, loaded at no more than 5% of the column volume on a 0.9×18 cm Sephadex G-50 column at the linear elution speed of 3 cm/hr. The elution was carried out at room temperature, and one-milliliter fractions eluting from the column at between 0.4 and 0.6 times the total chromatographic bed volume were collected. These fractions were tested for SCM activity. The SCM-active fractions were contained within the first elution peak as determined by optical densities of the one-milliliter fractions after testing of the fractions in the SCM test.

Once the fractions were tested for SCM activity, the active fractions from the same cancer types were pooled and lyophilized.

For further purification the lyophilized samples were dissolved in 10 mM $NH_4HCO_3$ and loaded at no more than 4% of the column volume on an 0.8×26 cm column of Whatman DE-52 microgranular DEAE-cellulose. The column was washed with 10 ml of 10 mM aqueous $NH_4HCO_3$ increasing by 0.108% per minute from 10 mM to 1M $NH_4HCO_3$. One-milliliter fractions were collected and the optical absorption at 220 nm was determined for each fraction. Based on the optical absorbance, active fractions eluting from the column at between 4.5 and 4.7 times the total chromatographic bed volume were pooled and lyophilized for testing and further purification. These fractions showed SCM activity when tested in the SCM test as described above. The SCM activity was specific for cancer, as lymphocytes from patients free of cancer did not respond to these fractions in the SCM test.

Example 3

Final Purification of SCM Factor of Example 3 by RP-HPLC

The DE-52 general cancer-associated SCM-active fractions of Example 3 were then reconstituted and purified to homogeneity by reverse phase high pressure liquid chromatography (RP-HPLC) using a 2.1 mm×22 cm HPLC column. The column was packed with Aquapore RP-300™ (7 microns). The mobile phases used in the RP-HPLC purification step were as follows:

Phase A: 0.1 volume percent aqueous trifluoroacetic acid (TFA).

Phase B: 0.09 volume percent aqueous TFA in aqueous 70% acetonitrile.

Lyophilized DE-52 SCM-active fractions were reconstituted with sterile water for injections (without preservatives) and 250 microliter aliquots were injected into the RP-HPLC column. The mobile phase flow rate was 50 microliters per minute and its composition profile was 10 minutes of 90 volume percent of Phase A, 10 volume percent of Phase B, followed by 30 minutes of linear increase of Phase B at the rate of 3 volume percent per minute. The optical density peaks detected by optical absorbance at 220 nm were hand-collected via a "nanobore" teflon tubing into 1.5 ml plastic conical Eppendorf centrifuge tubes and the solvent was evaporated in a vacuum centrifuge. In all cases, the general cancer-associated SCM-recognition factor eluted from the column at 74 volume percent of Phase B. The eluted SCM factor had activity in the SCM test. The activity was specific for cancer, as lymphocytes from patients free of cancer did not respond in the SCM test to the eluted fraction.

Example 4

Alternative RP-HPLC Purification of SCM Factor

Alternatively, the SCM factor can be purified by performing HPLC using a 4.6 mm×25 cm HPLC column packed with Ultrasphere ODS™ (5 microns) distributed by Beckman Instruments, Inc. with the DEAE-52 SCM-active fractions of Example 3. The mobile phases used with this column were as follows:

Phase A: 0.1 volume percent aqueous trifluoroacetic acid (TFA).

Phase B: 0.1 volume percent TFA in aqueous 70% acetonitrile.

The same general procedure was followed with this column as for the Aquapore column, except that the mobile phase flow rate was 1.00 ml per minute and its composition profile was 5 minutes of 70 volume percent of Phase A, 30 volume percent of Phase B, followed by 20 minutes of linear increase of Phase B at the rate of 3.5 volume percent per minute. The optical density peaks were detected at 220 nm and were hand-collected into siliconized glass test tubes and the solvent was evaporated in a vacuum centrifuge. When this HPLC system was used, in all cases the purification of general cancer-associated SCM-recognition factor from nineteen different cancer types, including squamous cell carcinoma of the cervix, adenocarcinoma of the breast, adenocarcinoma of the bronchus, and malignant melanoma, always yielded a single optical density peak of activity, eluting at 56.3 volume percent of Phase B. This activity was cancer-specific.

Example 5

Identification and Isolation of SCM-Active Tryptic Peptides from SCM Factor Purified from Blood Plasma of Patients with Breast Cancer and Lung Cancer Tryptic peptides with SCM activity were isolated from the purified SCM factors isolated from blood plasma of patients with breast cancer or lung cancer. The cleavage of the purified factors with trypsin and purification of the active fragments were carried out by the following procedure:

To prevent adsorption loss of the peptide during lyophilization, the SCM factor was digested with trypsin in the presence of HPLC eluants. Trypsin digestion was carried out in 0.1M Tris-HCl buffer, pH 8.3, at 37° C. for 24 hours using 10 percent by weight of trypsin. The digest was diluted fourfold with 0.1 volume percent aqueous trifluoroacetic acid, and was injected into an Applied Biosystems 130 A microflow HPLC-separation system. The tryptic fragments were separated using an Aquapore RP-300 column (200 mm×2.1 mm). For the elution of the fragments, the mobile phase solvents were:

Phase A: 0.1 volume percent aqueous trifluoroacetic acid (TFA).

Phase B: 0.09 volume percent TFA in aqueous 70% acetonitrile.

The mobile phase flow rate was 50 μl per minute and the composition profile was 10 minutes of 96 volume percent Phase A, 4 volume percent Phase B, followed by a linear elution gradient comprising a 30 min linear increase in Phase B at a 3 volume percent per minute rate. The SCM-active tryptic peptide fragment eluted at 69.6 volume percent of Phase B and 30.4 volume percent of Phase A in a total volume of about 30 microliters.

The tryptic peptide cleaved from the SCM factor purified from patients with lung cancer was tested for SCM activity and found to be fully active. By comparison with the sequences of the entire isolated SCM factors determined in Example 6, these tryptic peptides were found to represent amino acids 8–22 of the SCM factor molecule.

Example 6

Amino Acid Sequences of Isolated SCM Factors

The amino acid sequences of isolated SCM factors, determined from purified preparations from blood plasmas of 12 different cancers, are presented in Table 1. The sequences were determined by an automated Edman degradation procedure, using the Applied Biosystems 477 A protein sequencer coupled with an online 120 A PTH-amino acid analyzer. Sequence-calling software was used to establish the amino acid residue at each cycle. The sequences of the SCM-factor peptides were obtained in repetitive analyses of two to three different preparations, isolated and purified to homogeneity, from pooled blood plasmas of about 5 to 50 different patients with a diagnosis of the same type of cancer. Amino acid residues designated in brackets below the primary, most significant residue detected at the particular degradation cycle represent secondary amino acid residues present in some of the degradation cycles in significant amounts. These secondary residues may indicate the presence of genetic polymorphisms of the SCM factors from individual blood donors contained in the sample pool that was used for sequencing; many, but not all, of the substitutions in these polymorphisms are conservative substitutions. In two cases, where a total of 35 amino acids were seen, the last six were weak. This indicates that two separate factors were present in the preparations, one of 29 amino acids, and a second of up to 35 amino acids. These two preparations were from donors with cancer of the prostate and seminoma of the testes. In some cases, no amino acid was seen in a particular cycle, designated by "X." These amino acids are most likely cysteine, and are otherwise referred to as cysteine (C). This is because of the 20 common amino acids, cysteine is the only one not detectable by the Edman degradation procedure.

TABLE 1

| AMINO ACID SEQUENCES OF PURIFIED ISOLATED SCM FACTORS |
|---|
| Ca-BREAST:     10     20     30<br>V I P P E V K F N K P F V F L M I D Q N T K T P L F M G K (SEQ ID NO: 14)<br>(M)                           (V) |
| Ca-LUNG:     M I P P E V K F N K P F V F L M I D Q N T K V P L F M G K (SEQ ID NO: 6)<br>                         (T) |
| Ca-COLON:     M I P P E V K F N K P F V F L M I D Q N T K V P L F M G K (SEQ ID NO: 6)<br>       (D) |
| MELANOMA:     M I P P E V K F N K P F V F L M I D Q N T K X P X F M G X (SEQ ID NO: 15) |

TABLE 1-continued

AMINO ACID SEQUENCES OF PURIFIED ISOLATED SCM FACTORS

| | |
|---|---|
| SCC-CERVIX: | M I P P E V K F N K P F V F L M I D Q N T K V P L F M G K (SEQ ID NO: 6)<br>(S) |
| Ca-OVARY: | M I P P E V K F N K P F V F L M I D Q N T K X X L F M G K (SEQ ID NO: 16)<br>(V) |
| Ca-UTERUS: | R I P P E V K F N K P F V F L M I D Q N T K R P L F M G K (SEQ ID NO: 17)<br>(S) |
| Ca-PANCREAS: | V I P P E V K F N K P F V F L M I D Q N T K X P L F M G K (SEQ ID NO: 18) |
| Ca-RENAL: | V I P P E V K F N X P F V F L M I D Q N T K V P L F M G K (SEQ ID NO: 19) |
| Ca-GASTRIC: | R I P P E V K F N K P F V F L M I D Q N T K X P X F M G X (V V N X T E) |
| (SARCOMA) | (S)      W (SEQ ID NOS: 20 & 21) |
| Ca-PROSTATE: | V I P P E V K F N K P F V F L M I E Q N T K S P L F M G K (V V N P T Q)<br>(S)      W (SEQ ID NOS: 22 & 23) |
| Ca-TESTIS:<br>(SEMINOMA) | S I P P E V K F N K P F V F L M I E Q N T K S P L F M G K V V N P T Q<br>(V)(SEQ ID NO: 24) |

Example 7

SCM Activity of Synthetic SCM Factor

A synthetic SCM factor, representing the "consensus sequence" of M-I-P-P-E-V-K-F-N-K-P-F-V-F-L-L-I-D-Q-N-T-K-V-P-L-F-M-G-K (SEQ ID NO: 6), was synthesized using conventional solid-phase peptide synthesis techniques. Such techniques are described, for example, in M. Bodanszky, "Peptide Chemistry" (Springer-Verlag, Berlin, 1988), Ch. 10, "Solid Phase Peptide Synthesis."

The SCM activity of this synthetic SCM factor was tested by the standard SCM test. The synthetic SCM factor was fully active in the SCM test; this activity was specific for lymphocytes from cancer patients.

Example 8

Fragments of Synthetic SCM Factor

Peptides representing distinct fragments of the synthetic SCM factor of Example 15 were synthesized by conventional solid-phase peptide synthesis techniques. These peptides were designated F1-F5 and have the following sequences:

F1: M-I-P-P-E-V-K-F-N-K-P-F-V-F-L-M-D-Q-N-T-K (SEQ ID NO: 7);

F2: F-N-K-P-F-V-F-L-M-I-D-Q-N-T-K-V-P-L-F-M-G-K (SEQ ID NO: 1);

F3: F-N-K-P-F-V-F-L-M-I-D-Q-N-T-K (SEQ ID NO: 8);

F4: F-L-M-I-D-Q-N-T-K (SEQ ID NO: 5); and

F5: M-I-P-P-E-V-K-F-N-K-P-F-V-F (SEQ ID NO: 9).

These fragments represented the following portions of the complete synthetic SCM molecule: F1, amino acids 1–22; F2, amino acids 8–29; F3, amino acids 8–22; F4, amino acids 14–22; and F5, amino acids 1–13.

Fragments F1, F2, F3, and F4 were all fully active in the SCM test, while fragment F5 was inactive. For fragments F1 through F4, the expected specificity of the SCM response was maintained, as these fragments gave no decrease in fluorescence polarization when used to challenge lymphocytes isolated from donors free of malignancy.

Example 9

Preparation of Antibodies to Synthetic SCM Factor

The synthetic SCM factor molecule was used to immunize experimental animals. Both pure synthetic SCM-factor molecules and SCM conjugated to the carrier keyhole limpet hemocyanin (KLH) via an added carboxy-terminal cysteine using N-succinimidyl bromoacetate as the cross-linking agent. These immunogens were used to immunize female New Zealand rabbits. Both immunogens were diluted for primary immunization to 1.0 mg/ml with sterile PBS, combined with an equal volume of Freund's complete adjuvant, and emulsified. For primary immunization, a total of 25 μg or 50 μg of either synthetic SCM factor or synthetic SCM factor conjugated with KLH (SCM-KLH) was injected into each rabbit; two rabbits were used for each dose range. The inoculate was administered at 0.2 ml into two legs intramuscularly and over a minimum of 12 dorsal sites subcutaneously at 0.2 ml per site. One month later, the first booster injection was administered. Synthetic SCM factor and SCM-KLH were each administered with an equal-volume mixture of Freund's complete and incomplete adjuvants and emulsified. The booster inoculates were injected via intramuscular and subcutaneous sites similar to those used for primary inoculations. Total doses of 25 μg or 50 μg of immunogen per rabbit were administered in the booster injections. The injections of SCM factor were not toxic to the immunized animals, as no ill effects were seen in immunized animals.

Blood samples taken 10 weeks after primary immunization yielded antisera containing higher amounts of immunoglobulins (IgG) from those animals injected with 50 μg of immunogen than from those animals injected with 25 μg of immunogen. Radial immunodiffusion tests, conducted as described in W. Becker, "Determination of Antisera Titres Using the Single Radial Immunodiffusion Method," *Immunochemistry* 6, 539 (1969), gave precipitation reactions against the unconjugated SCM factor and SCM factor conjugated to bovine serum albumin (BSA).

After further booster immunizations, all animals continued to yield positive antisera.

To separate the immunoglobulins containing the desired antibodies from the antisera, the immunoglobulins were first precipitated with an equal volume of saturated ammonium sulphate. The precipitates were then dissolved in 0.9% NaCl.

To remove ammonium sulfate, the antibody-containing solutions were either dialyzed or ultrafiltered 10 times through an Amicon™ membrane filter with a 5000-dalton molecular weight cutoff. Antibodies were kept frozen at −40° C. until use or affinity purification.

Affinity purification of antibodies was carried out, for antibody prepared to the entire 29-amino-acid synthetic SCM factor, on avidin-agarose gels (Pierce Chemical Company, Rockford, Ill.) by coupling the biotinylated antigen, against which the antibody was raised, via the avidin-biotin interactions.

Example 10

Effect of the Isolated SCM Factor on Natural Killer (NK) Activity

To demonstrate the effect of the isolated SCM factor on the natural cytotoxicity of potentially SCM-responding lymphocytes toward malignant cells, such lymphocytes obtained from healthy donors were incubated for 2.5 hr at 37° C. with plasma containing SCM factor isolated as previously described from blood samples of donors afflicted with cancer. Aliquots of these lymphocytes were also retained as controls and not incubated. In addition, potentially SCM-responding lymphocytes were obtained from donors having cancer, and treated in the same manner—some aliquots incubated with plasma containing SCM factor and others retained as controls and not incubated.

After incubation the cytotoxicity of the lymphocytes was tested in accordance with the method described in M. R. Potter and M Moore, "Natural Cytotoxic Reactivity of Human Lymphocyte Subpopulations," *Immunology* 37, 187–194 (1979). In accordance with this published method cells of the K 562 human myeloid cell line labeled with $^{51}$Cr were used as target cells for the assay. The potentially SCM-responding lymphocytes were used as the effector cells. The ratio of target cells to effector cells was 1 to 20. Release of the $^{51}$Cr indicates that the effector cells are toxic to the target cell. The percent of cytotoxicity is determined as follows:

$$\text{Percent cytotoxicity} = \frac{R_S - R_C}{R_T - R_C} \times 100$$

where $R_S$ is the percent of $^{51}$Cr release in the sample, $R_C$ the percent of $^{51}$Cr release in the control and $R_T$ is the percent of $^{51}$Cr release in the presence of a detergent, Triton X-100. The results are shown in Table 2. These results show that incubation of potentially SCM-responding lymphocytes from healthy donors for 2.5 hr with ultrafiltrates filtered through filter with a nominal 1000-dalton molecular weight cutoff decreased their cytotoxicity by over 90%. When the incubation was performed with potentially SCM-responding lymphocytes from cancer patients, the decrease in cytotoxicity was smaller, between 40 and 90%. However, such lymphocytes from cancer patients had lower levels of cytotoxicity before incubation, and the residual level of cytotoxicity remaining after incubation with ultrafiltrate was comparable to that remaining after incubation of lymphocytes from healthy donors. The lower level of cytotoxicity present in cells from cancer patients was consistent with a decrease of such cytotoxicity caused by in vivo exposure to factors such as the cancer-associated SCM recognition factor.

TABLE 2

EFFECT OF SCM FACTOR ON NATURAL KILLER ACTIVITY
AGAINST K 562 HUMAN MYELOID CELL LINE
(EXAMPLE 10)

| Diagnosis of Donor of Potentially SCM-Responding Lymphocytes | Diagnosis of Donor of SCM Factor as Ultrafiltrate | % Cytotoxicity of Lymphocytes: | | % Decrease in Cytotoxicity |
|---|---|---|---|---|
| | | Before Incubation | After Incubation | |
| Healthy Donor #1 | Ca-Cervix | 40.0 | 2.2 | 94.5 |
| Healthy Donor #2 | Ca-Bronchus | 30.0 | 1.7 | 94.3 |
| Healthy Donor #3 | Ca-Larynx | 11.0 | 0.76 | 93.1 |
| Healthy Donor #4 | Ca-Larynx | 22.0 | 2.2 | 90.0 |
| Healthy Donor #5 | Ca-Pharynx | 41.0 | 0.33 | 99.2 |
| Ca-Tongue | Ca-Larynx | 23.0 | 2.1 | 90.9 |
| Ca-Lip | Ca-Bronchus | 7.4 | 2.7 | 63.5 |
| Ca-Ovary | Ca-Bronchus | 10.0 | 6.1 | 39.0 |
| Ca-Cervix | Ca-Cervix | 25.2 | 1.5 | 94.0 |
| Ca-Bronchus | Ca-Cervix | 29.6 | 3.1 | 89.5 |

Example 11

Effect of the Synthetic SCM-Factor Peptide on Natural Killer (NK) Activity

The effect of the synthetic SCM-factor peptide (Example 7) on natural killer (NK) activity was determined. Human K562 myeloid cells were used as targets for NK effector lymphocytes. The cells were obtained from the American Type Culture Collection (ATCC) and were grown in RPMI-1640 medium, supplemented with fetal bovine serum (FBS) and antibiotics as recommended. Before use in cytotoxicity experiments, the viability of the harvested, washed cells was tested by the trypan blue exclusion test. The NK activity of effector lymphocytes was assessed by the $^{51}$Cr release cytotoxicity assay as described by M. R. Potter & M. Moore, supra. In this assay, $2 \times 10^6$ K562 cells suspended in RPMI-1640 medium with 10% FBS were labelled for 90 minutes at 37° C. with 100 μCi sodium [$^{51}$Cr]chromate (Amersham Corp., Arlington Heights, Ill.). The labelled target cells were washed four times in RPMI-1640 medium and resuspended in RPMI-1640 medium containing 10% FBS at $5 \times 10^4$ cells/ml. Samples of 200 μl, containing $10^4$ K562 cells, were delivered into 2.5-ml plastic tubes.

The lymphocytes used as effector cells in this example were either peripheral blood lymphocytes (PBL) or the SCM-responding lymphocyte fraction of PBL. The peripheral blood lymphocytes were obtained by centrifugation of heparinized blood on Histopaque 1077 density solution (Sigma Diagnostics, St. Louis, Mo.).

For isolation of the SCM-responding subset of PBL, lymphocytes collected from the interphase of the centrifugation were washed and suspended in 0.9% preservative-free sodium chloride solution for injections (LymphoMed Inc., Rosemont, Ill.), and layered on a stack of Percoll (Pharmacia LKB, Inc., Piscataway, N.J.) density solutions of 0.320 Osm/kg encompassing the upper (1.0670 g/cm$^3$ at 20° C.) and lower (1.0590 g/cm$^3$ at 20° C.) buoyant density interval of SCM-responding lymphocytes. After centrifugation at 1100×$g_{AV}$ for 20 minutes, the SCM-responding lymphocytes were collected from the interphase between the density solutions. The isolated cells were washed in 0.9% saline and twice in phosphate buffered saline (PBS) and resuspended in PBS at 2×10$^6$ cells/ml. The SCM-responding subpopulation of PBL was up to 88% enriched in NK cells, as determined by anti-Leu-11c, CD16 and anti-Leu-19, CD56 antibodies (Becton Dickinson Immunocytometry Systems, Mountain View, Calif.).

For use as effector cells, the collected PBL were washed once in 0.9% sodium chloride solution and twice in complete Dulbecco's phosphate buffered saline (Gibco, Life Technologies Inc., Grand Island, N.Y.).

Aliquots of effector cells were incubated with 35 femtomoles of synthetic SCM factor per lymphocyte for 3 hours at 37° C. Other aliquots, for controls, were not incubated. For determination of the effect of the SCM-factor on cytotoxicity, 200-μl aliquots of the control or treated effector lymphocytes, suspended in PBS, were added to each tube containing labelled target cells and spun for 5 minutes at 200×$g_{AV}$. Effector cell to target cell ratios of 40:1 were used. Control tubes containing 200 μl of target cells and 200 μl of PBS were included to determine spontaneous $^{51}$Cr release. All cytotoxicity assays were carried out in triplicate for 18 hours at 37° C. in an atmosphere of 95% air and 5% CO$_2$. At the end of the incubation, the tubes were centrifuged at 300×$g_{AV}$ for 10 minutes. A 200-μl aliquot of the supernatant was removed from each tube. The aliquots were counted on a Beckman gamma counter 5500B (Beckman Instruments, Inc., Fullerton, Calif.). The percentage $^{51}$Cr release was determined for each tube, and using the mean value for the triplicate tubes, the percentage cytotoxicity was calculated according to the following equation:

$$\text{Percent cytotoxicity} = \frac{R_S - R_C}{R_T - R_C} \times 100$$

The spontaneous, control $^{51}$Cr release was between 10% and 15%. The maximum $^{51}$Cr release was taken as 100%.

In some cases, the effect of washing on lymphocytes incubated with the synthetic SCM factor was investigated. In these cases, the cells were washed three times with PBS and then resuspended in PBS for the subsequent cytotoxicity assay. The viability of both the control and the SCM factor-treated lymphocytes, as determined by the trypan blue exclusion test, was greater than 95%.

The effect of the SCM-factor peptide on the NK activity of peripheral blood lymphocytes (PBL) and the SCM-responding subpopulation of lymphocytes is shown in Table 2. At the effector cell to target cell ratio of 40:1 in an 18-hour assay, the percentage cytotoxicity of both the PBL and the SCM-responding lymphocyte effectors was suppressed by at least 97% after incubation with 35 femtomoles of the SCM-factor peptide per cell. The NK-suppression effect of the SCM-factor peptide was not reversed by washing the treated lymphocytes three times before the cytotoxicity assay. The results in FIG. 1 show that under identical experimental conditions, the cytotoxicity, in the absence of incubation with SCM-factor peptide, decreased with decreasing effector-to-target cell ratios. However, when lymphocytes were treated with 35 femtomoles of the SCM-factor peptide per cell, the cytotoxicity was suppressed to the same very low level regardless of the effector-to-target cell ratios and the molarity of the SCM-factor peptide solutions, which vary between 70 μmole/1 and 7 μmole/1.

Figure 2:
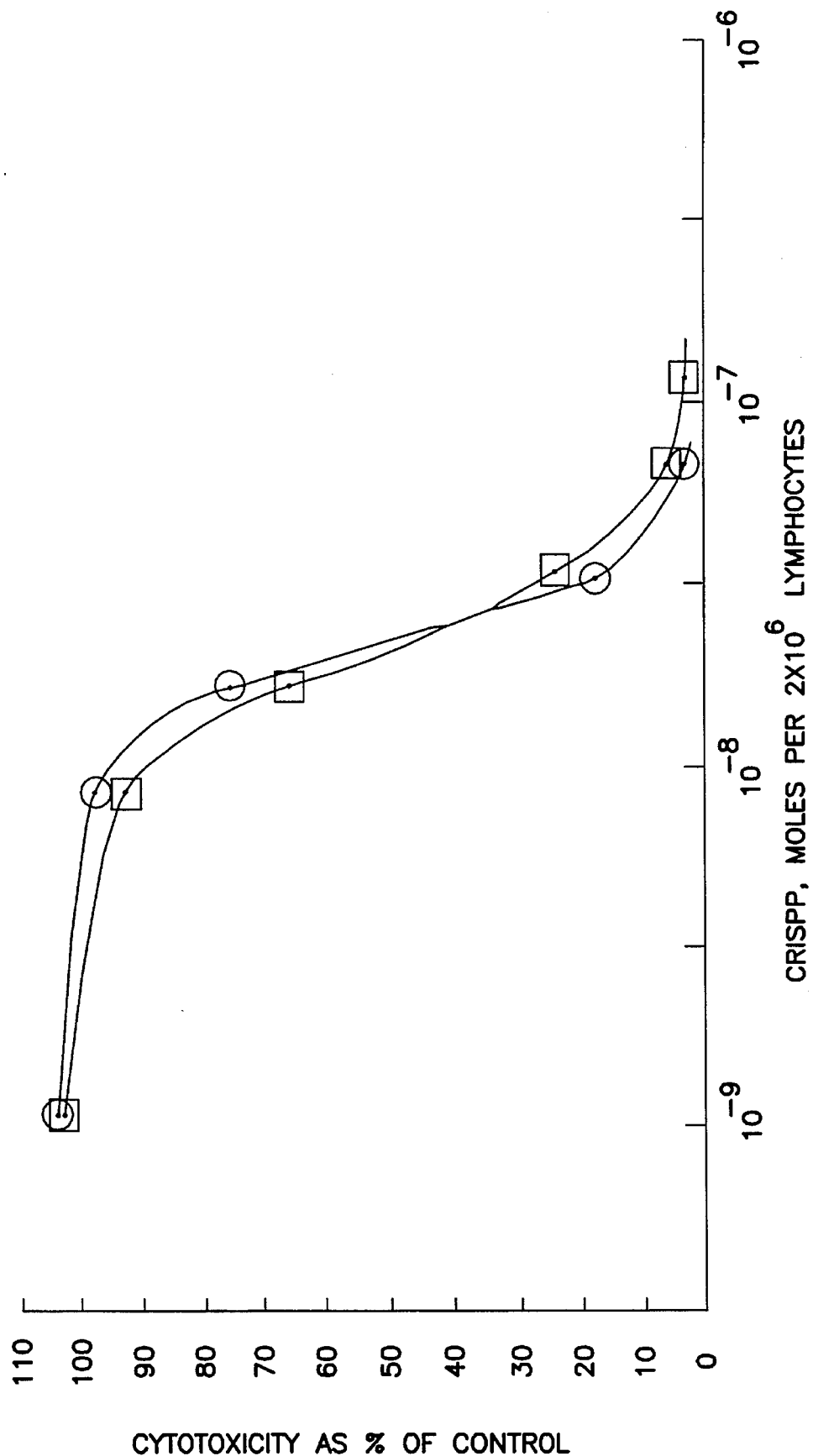
FIG. 2 is a graph showing the NK-suppressive effect of the intact 29-amino-acid synthetic SCM-factor peptide and a fragment comprising residues 8–29 of the synthetic SCM-factor peptide as a function of the quantity of peptide or fragment per lymphocyte.

FIG. 2 shows a dose response curve for suppression of NK cytotoxicity by the synthetic SCM factor peptide. The results show that for a 50% decrease of cytotoxicity, only 12 femtomoles of the synthetic SCM-factor peptides per lymphocyte is required.

The results in Table 4 show the dose-time dependence of the effect of the SCM-factor peptide on the suppression of NK effector cell cytotoxicity against K562 target cells. Incubation of PBL with only 3.5 femtomoles of synthetic SCM-factor peptide per lymphocyte for 3 hours only slightly decreased their killing efficiency. However, after 23 hours of incubation, the percent of cytotoxicity decreased to only 60% of the control. The long incubation time did not effect the NK activity for control aliquots not incubated with SCM-factor peptide. The viability of control and SCM-factor peptide-treated cells remained greater than 90%.

TABLE 3

EFFECT OF THE SYNTHETIC SCM-FACTOR PEPTIDE ON THE NATURAL KILLER (NK) ACTIVITY OF SCM-RESPONDING LYMPHOCYTES AND PBL AGAINST HUMAN K562 MYELOID TARGET CELLS

| | Percent Cytotoxicity | | |
|---|---|---|---|
| Effector Lymphocytes | Control | After Treatment with SCM-Factor Peptide[c] | After Treatment with SCM-Factor Peptide, Washed 3× with PBS |
| SCM-Responding[a] | 84.0 ± 3.0 | 0.1 ± 0.9 | 0.1 ± 0.9 |
| SCM-Responding | 72.0 ± 2.8 | 0.8 ± 0.7 | — |
| SCM-Responding | 45.6 ± 2.7 | 0.1 ± 0.8 | — |
| PBL[b] | 77.8 ± 2.5 | 1.2 ± 1.0 | — |
| PBL | 72.7 ± 1.2 | 3.2 ± 0.7 | 3.0 ± 0.8 |
| PBL | 80.4 ± 1.8 | 2.6 ± 0.9 | 2.4 ± 1.0 |

[a]SCM-responding lymphocytes comprise a density-specific subpopulation of peripheral blood lymphocytes containing between 60% and 80% of D56+ and D16+ NK cells.
[b]Isolated on Histopaque 1077 density solution without further purification.
[c]SCM-factor peptide used at 35 femtomoles/lymphocyte for 3 hours at 37° C. The effector cell: target cell ratio is 40:1. All values are means of triplicate tests.

TABLE 4

EFFECT OF TIME OF INCUBATION WITH SYNTHETIC SCM-FACTOR PEPTIDE ON NK ACTIVITY OF PBL AGAINST HUMAN K562 MYELOID TARGET CELLS

| Treatment | % Cytotoxicity | Cytotoxicity as % of Control |
|---|---|---|
| Control PBL[a] | 58.6 ± 0.4 | 100.0 |
| PBL + SCM Factor (3 hr. Incubation) | 56.5 ± 2.0 | 96.6 |
| PBL + SCM Factor (23 hr. Incubation) | 35.2 ± 0.5 | 60.2 |

[a]Control PBL incubated for 23 hours under identical conditions in RPMI-1640 medium.
SCM factor was used at 3.5 femtomoles/lymphocyte. The effector cell-target cell ratio was 40:1. The values are means of triplicate tests.

Example 12

Identification of the Domain of the Synthetic SCM-Factor Peptide Responsible for NK Suppression The results of incubation of PBL effector lymphocytes with the synthetic SCM-factor peptide and with fragments representing various portions of the synthetic SCM-factor peptide are shown in Table 5. There are two peptides with NK-suppression effects: The entire SCM-factor peptide, with 29 amino acids, and a peptide fragment corresponding to amino acid residues 8–29 of the complete synthetic SCM-factor peptide. This latter region encompasses the domain of the synthetic SCM-factor peptide responsible for NK suppression. Comparison of the results with fragment F2 (residues 8–29) and F3 (residues 8–22) shows that at least some of the residues between residue 22 and 29 are required for NK suppression. Similarly, a comparison of the results obtained with fragment F2 with those of fragment F7 (residues 14–29) indicates that at least some of the residues between amino acid 8 and amino acid 14 are required for NK suppression.

The results in FIG. 2 show that fragment F2, comprising residues 8–29, was as effective in inducing NK suppression as the entire synthetic SCM-peptide, when a dose-response curve is determined for the two peptides.

TABLE 5

IDENTIFICATION OF THE DOMAIN OF THE SYNTHETIC SCM-FACTOR PEPTIDE RESPONSIBLE FOR NK SUPPRESSIVE ACTIVITY

| | Percent Cytotoxicity After Treatment with: | | | | | | | |
|---|---|---|---|---|---|---|---|---|
| Control | SCM Factor (1–29) | F1 (1–22) | F2 (8–29) | F3 (8–22) | F4 (14–22) | F5 (7–13) | F7 (14–29) | F8 (23–29) |
| 72.7 | 3.2 | 78.5 | 14.9 | 74.5 | 76.2 | 72.7 | — | — |
| 80.4 | 3.1 | 81.0 | 2.6 | 80.5 | 81.0 | 79.8 | — | — |
| 46.5 | 0.1 | — | 2.4 | — | 48.6 | — | — | — |
| 71.2 | — | — | — | — | — | — | 72.7 | 71.7 |
| 31.0 | — | — | — | — | — | — | 32.0 | 33.0 |

PBL effector cells were used, with K562 target cells at an effector cell-target cell ratio of 40:1. PBL were incubated for 3 hours with 35 femtomoles of the intact synthetic SCM-factor peptide or fragments encompassing the indicated regions of the peptide. All values are means of triplicate tests. The standard deviations range from ± 0.1 to ± 2.0.

Example 13

Effect of the Synthetic SCM-Factor Peptide on Lymphokine-Activated Killer (LAK) Activity To determine the effect of the synthetic SCM-factor peptide on lymphokine-activated killer (LAK) activity, the cytotoxicity assay was performed using NK-resistant, LAK-sensitive human Daudi Burkitt lymphoma cells as targets. The effector cells were PBL. The PBL effectors suspended in RPMI-1640 medium with 10% FBS at a concentration of $2 \times 10^6$ cells/ml were divided into two lots. One-third was kept as the NK control and two-thirds were incubated with 1,000 units of human recombinant interleukin-2 (rIL-2) (Genzyme Corp., Boston, Mass.) per milliliter for 18 hours. The control and incubated samples were placed in the incubator at 37° C. in an atmosphere of 95% air and 5% $CO_2$. The rIL-2 incubated sample was then divided into two aliquots. One aliquot was kept as the LAK control sample and the second rIL-2 treated aliquot was further incubated for 3 hours with 35 femtomoles of the synthetic SCM-factor peptide per lymphocyte at 37° C. on a shaker at 180 rpm. The viability of the effector lymphocytes was assessed by the trypan blue exclusion test and was found to be over 90% for all effector lymphocyte samples.

The results are shown in Table 6. The controlled cytotoxicity obtained in a 4-hour assay at an effector-to-target cell ratio of 40:1 was only 13.5%. After incubation of PBL effectors with rIL-2 for 18 hours, the killing efficiency of the cells from the same donor was augmented; the cytotoxicity against Daudi cells increased to 77.5%, i.e., 574% of the control cytotoxicity. Incubation of LAK cells with 3 hours with 35 femtomoles of the SCM-factor peptide per cell decreased the r-IL-2 induced LAK cytotoxicity against Daudi cells to 3.4%, i.e., 25.2% of the original control NK cytotoxicity.

These results show that the SCM-factor peptide can block not only NK activity, but also LAK activity of PBL lymphocytes.

TABLE 6

EFFECT OF THE SYNTHETIC SCM-FACTOR PEPTIDE ON CYTOTOXICITY OF rIL-2 ACTIVATED PBL AGAINST DAUDI TARGET CELLS

| Treatment of Lymphocytes (PBL) | % Cytotoxicity | Cytotoxicity as % of Control |
|---|---|---|
| Control PBL | 13.5 ± 1.1 | 100.0 |
| PBL + rIL-2 (18 hrs.) → wash | 77.5 ± 2.8 | 574.0 |
| PBL + rIL-2 (18 hrs.) → wash + SCM Factor (3 hrs.) | 3.4 ± 7 | 25.2 |

The SCM factor was used at 35 femtomoles per lymphocyte. The effector cell-target cell ratio was 40:1. The cytotoxicity was 4 hours. Values are means of triplicate tests.

Example 14

Effect of the Synthetic SCM-Factor Peptide on Target-Effector Conjugate Formation The first step of the mechanism of cancer cell killing by lymphocytes is the attachment of effectors to target cells. The effect of the synthetic SCM-factor peptide on this step was investigated by scoring conjugate-forming target cells under the microscope.

The effector-target cell conjugate formation assay was carried out as described by Chow and Jondal, "A Central Role for Phosphoinositide Hydrolysis in Activating the Lytic Mechanism of Human Natural Killer Cells," *Immunology* 70:106–110 (1990). The effector lymphocytes were washed and suspended in PBS at $2 \times 10^6$ cells/ml. Half was used as a control and the second half was incubated with 35 femtomoles of synthetic SCM-factor peptide per lymphocyte for 3 hours at 37° C. on a shaker. The effector cells were washed twice in PBS and resuspended in RPMI-1640 with 10% FBS. The K562 target cells were harvested and washed in RPMI-1640 with 10% FBS. The effector and target cells were combined at a 1:1 cell number ratio, centrifuged for 5 minutes at $100 \times g_{AV}$ and incubated at 37° C. for 10 minutes. The pellet was resuspended gently and the effector-target cell conjugates were scored using the Reichert Ultrastar microscope (Reichert, Vienna, Austria), with the oil-immersion objective at an overall magnification of 400. On each slide, 300–500 target cells were counted for control and SCM-factor-peptide-treated samples. Seven experiments using lymphocytes from three different healthy donors were carried out. The mean percentage of conjugates scored was 21.6% ±3.64% in control and 21.5 ±2.96% in the SCM-factor treated samples, indicating that binding of NK lymphocytes to target cells was not affected by the SCM-factor peptide.

Example 15

Inhibition of Interleukin-2 (IL-2) and Tissue Necrosis Factor α (TNFα) Released from Lymphocytes by Synthetic SCM-Factor Peptide Release of IL-2 from lymphocytes in the presence of K562 target cells was determined by an enzyme-linked immunosorbent assay (ELISA) ("Intertest-2", Genzyme Corp., Boston, Mass.). Lymphocytes (PBL) were isolated by density gradient (Histopaque 1077) centrifugation from heparinized blood, washed twice in 0.9% preservative-free sodium chloride, and once with complete PBS and resuspended in 3 ml of PBS at $1-3 \times 10^7$ cells/ml. The sample was divided into 3 aliquots in 3 separate tubes. Two samples were kept as controls and the third sample was incubated at 37° C. for 3 hours with the synthetic SCM-factor peptide at 35 femtomoles per lymphocyte. All samples were washed with 0.9% saline and resuspended in PBS at $9 \times 10^5$ cells/ml. Aliquots of K562 cells (1 ml), suspended in RPMI-1640 with 10% FBS at $5.1 \times 10^6$ cells/ml, were then added to one of the control sample tubes and the lymphocytes treated with the synthetic SCM-factor peptide. All cell suspensions were centrifuged at $200 \times g_{AV}$ for 5 minutes and incubated for 18 hours at 37° C. in an atmosphere of 95% and 5% $CO_2$. The next day all samples were centrifuged for 10 minutes at $300 \times g_{AV}$, 500-μl aliquots of the supernatant were collected, and the IL-2 content was determined using the ELISA assay following the manufacturer's instructions.

The same experimental procedure was used for determining release of TNFα for lymphocytes before and after treatment with the synthetic SCM-factor peptide. The TNFα released into the supernatant was determined by a quantitative EIA ("UBI™ TNFα EIA", Olympus Corp , Lake Success, N.Y.), following the manufacturer's instructions.

The results are shown in Table 7. Incubation of lymphocytes with 35 femtomoles of the synthetic SCM-factor for 3 hours decreased the release of IL-2 by 30% and that of TNFα by 78.6% after an 18-hour incubation of lymphocytes with K562 target cells at the effector-to-target ratio of 1:1.

TABLE 7

INHIBITION OF IL-2 AND TNFα RELEASE FROM LYMPHOCYTES BY THE SCM-FACTOR PEPTIDE

| Lymphocyte Product | Treatment Procedure | Product as % of Control |
|---|---|---|
| IL-2 | PBL + K562 Cells (18 hr.) | 100.0 |
| IL-2 | PBL + SCM Factor (3 hr.) + K562 Cells (18 hr.) | 70.9 |
| TNFα | PBL + K562 Cells (18 hr.) | 100.0 |
| TNFα | PBL + SCM Factor (3 hr.) + K562 Cells (18 hr.) | 21.4 |

Lymphocytes (PBL) were incubated with 35 femtomoles SCM-factor peptide per lymphocyte for 3 hours. Effector (PBL) to target (K562) cell ratios were 1:1. In case of IL-2 determination, PBL were washed before overnight incubation with K562 target cells. IL-2 and TNFα were determined by immunoassay as indicated. The net optical density of IL-2 and TNFα controls were 0.3251 and 1.798, respectively.

Example 16

Effect of Recombinant Interleukin-2 (rIL-2) on Lymphocytes Treated with Synthetic SCM-Factor Peptide It is known that interleukin-2 enhances the NK activity of lymphocytes. Therefore, PBL that had been incubated with SCM-factor were washed and subsequently incubated for 3 hours with either 1,000 units or 100 units of rIL-2.

The results are shown in Table 8. The subsequent incubation with rIL-2 did not restore the NK cytotoxicity of the lymphocytes that had been incubated with SCM factor. Indeed, cytotoxicity even decreased further.

TABLE 8

EFFECT OF rIL-2 ON SCM FACTOR-INDUCED SUPPRESSION OF NK ACTIVITY OF PBL AGAINST HUMAN K562 MYELOID CELLS

| Treatment of Effector PBL | % Cytotoxicity | Cytotoxicity as % of Control |
|---|---|---|
| Untreated Control PBL | 53.5 ± 3.0 | 100.0 |
| PBL + SCM Factor (3 hr.) → wash | 2.9 ± 0.4 | 5.4 |
| PBL + SCM Factor (3 hr.) → wash + 1000 U rIL-2 (3 hr.) | 0.3 ± 0.2 | 0.5 |
| PBL + SCM Factor (3 hr.) → wash + 100 U rIL-2 (3 hr.) → wash | 0.0 ± 0.3 | 0.0 |

The SCM-factor peptide was used at 35 femtomoles per lymphocyte. The effector cell-target cell ratio was 40:1.

Example 17

Reversal of NK Suppression Caused by Synthetic SCM-Factor Peptide by Autologous Blood Plasma To determine whether or not there existed any factor in blood plasma that could reverse the suppression of NK activity by SCM-factor peptide, PBL effector lymphocytes were incubated in autologous blood plasma. The PBL were divided into three samples, each containing $2 \times 10^6$ cells/ml suspended in PBS. One sample was kept as the NK control. The other two samples were incubated with 35 femtomoles per cell of the SCM-factor peptide for 3 hours at 37° C. on a shaker. Both samples were spun at $300 \times g_{AV}$ for 10 minutes, washed in 0.9% preservative-free sodium chloride, and resuspended in PBS. One of these samples was kept as the treated control. A second sample was washed, pelleted by centrifugation at 300×$g_{AV}$, and resuspended in fresh autologous cell-free blood plasma filtered through a 0.22 µm pore size nitrocellulose filter (Millipore Corp., Bedford, Mass.) for 3 hours at 37° C. with shaking. The cells were washed twice in 0.9% sodium chloride and resuspended in PBS at 2×10$^6$ cells/ml. The control, SCM-factor-peptide-treated sample, and the sample treated with autologous blood plasma were then used as effector lymphocytes in the cytotoxicity assay using K562 target cells to measure NK activity. The results are shown in Table 9.

TABLE 9

RESTORATION OF SCM-FACTOR-SUPPRESSED NK ACTIVITY OF LYMPHOCYTES BY AUTOLOGOUS BLOOD PLASMA

| Treatment of Effectors (PBL) | % Cytotoxicity | Cytotoxicity as % of Control |
|---|---|---|
| Donor A: | | |
| Control PBL | 62.1 ± 0.8 | 100.0 |
| PBL + SCM Factor (3 hr.) | 3.0 ± 1.1 | 4.9 |
| PBL + SCM Factor (3 hr.) + Plasma (3 hr.) | 48.0 ± 4.5 | 77.3 |
| Donor B: | | |
| Control PBL | 79.9 ± 1.6 | 100.0 |
| PBL + SCM Factor (3 hr.) | 3.0 ± 1.2 | 3.0 |
| PBL + SCM Factor (3 hr.) + Plasma (3 hr.) | 66.6 ± 1.9 | 83.4 |

SCM factor peptide was used at 35 femtomoles per lymphocyte. Autologous cell-free blood plasma was used. The effector cell-target cell (K562) cell ratio was 40:1. The cytotoxicity assays were for 18 hours.

The effect of the SCM-factor peptide on NK suppression could be substantially reversed by incubating lymphocytes for 3 hours in cell-free autologous blood plasma. In the two cases tested, the cytotoxicity of SCM-factor-treated lymphocytes increased from 4.9% to 77.3% and 3.0% to 3.4%, respectively, after treatment with the autologous blood plasma.

Example 18

Preparation of Antibodies to Residue 14–29 of Synthetic SCM-Factor Peptide

The fragment F2 of synthetic SCM-factor peptide (residues 14–29) was used to immunize experimental animals. The peptide was conjugated to the carrier keyhole limpet hemocyanin (KLH via an added carboxy-terminal cysteine using N-succinimidyl bromoacetate (Bernatowicz and Matsueda, supra) as the cross-linking agent. This immunogen was used to immunize a goat. The immunogen was diluted for primary immunization to 1.0 mg/ml with sterile PBS, combined with an equal volume of Freund's complete adjuvant and emulsified. For primary immunization, a total of 50 µg of the peptide fragment conjugated to KLH was injected into the goat, and immunization was performed generally as for intact 29-amino-acid SCM factor as in Example 9. The antibodies were affinity purified on avidin-agarose gels (Pierce Chemical Co., Rockford, Ill.) by coupling biotinylated antigen to the gel via the avidin-biotin interaction. The coupling and affinity purification were carried out as recommended by the manufacturer.

Example 19

Prevention of NK Suppression Caused by Synthetic SCM-Factor by Antibodies to Residues 14–29 of Synthetic SCM-Factor Peptide (Example 18)

To determine whether antibodies to a portion of the synthetic SCM-factor peptide could block the NK suppressive effect of SCM-factor peptide, a cytotoxicity assay was performed on PBL effector lymphocytes incubated with SCM-factor peptide together with the antibody. Aliquots of PBL suspended in RPMI-1640 medium were incubated with the SCM-factor peptide at a concentration of 35 femtomoles per lymphocyte in the presence and absence of the anti-SCM peptide fragment antibody for 3 hours at 37° C. on a shaker. An aliquot of lymphocytes was used as an untreated control. The cytotoxicity assay against K562 target cells was carried out as described above, except that only 10$^3$ K562 target cells per assay were used at an effector-to-target cell ratio of 10:1.

The results are shown in Table 10. The antibody to the fragment of the SCM-factor encompassing residues 14–29 completely prevented the suppression of NK cytotoxicity by the SCM-factor peptide.

TABLE 10

PREVENTION OF SCM-FACTOR NK SUPPRESSION BY ANTIBODY TO RESIDUES 14–29 OF SCM FACTOR

| Treatment of Effector PBL | % Cytotoxicity | Cytotoxicity as % of Control |
|---|---|---|
| Control PBL + K562 Cells | 16.3 ± 1.1 | 100.0 |
| PBL + SCM Factor (3 hr.) + K562 Cells | 0.2 ± 0.5 | 1.2 |
| PBL + SCM Factor + Anti-SCM Factor (14–29) Antibody + K562 Cells | 17.3 ± 0.3 | 106.0 |

SCM-factor was used at 35 femtomoles per lymphocyte. Affinity purified anti-SCM factor (14–29) antibody was used. The effector cell:target cell ratio was 10:1.

Example 20

Detection of Natural Anti-SCM Antibodies in Blood Plasma

To detect naturally occurring anti-SCM antibodies in blood plasma an ELISA assay was performed on blood plasma by binding synthetic SCM factor to plastic tubes, binding specific anti-SCM antibody occurring in blood plasma samples to the SCM factor bound by the tubes, and then detecting the anti-SCM antibody with a second anti-IgG antibody.

The tubes used were washed and soaked in 0.5 mole/l sodium carbonate overnight and then washed three times with 0.1 mole/l sodium carbonate. The washed tubes were then coated with 1 µg/ml of synthetic SCM factor peptide in 0.1 mole/l sodium carbonate, pH 9.8, for three hours at 37° C. on a shaker.

The tubes were then washed and post-coated with bovine serum albumin (BSA): 0.4% BSA in phosphate-buffered saline (PBS) without calcium and magnesium, pH 7.2, for three hours at room temperature. The tubes are then washed three times with incubation buffer (0.4% BSA in PBS without calcium and magnesium, pH 7.2, plus 0.05% Tween-20).

To begin the assay, 0.5 ml of incubation buffer was added to each tube. Triplicate samples of each blood plasma to be tested were taken (300 µl) and added to the tubes. The tubes were incubated for three hours at room temperature on a shaker. The tubes were then washed three times with 0.9% sodium chloride solution containing 0.05% Tween-20.

The second antibody was then added, either goat-anti-human IgG conjugated to horseradish peroxidase or rabbit-anti-human IgG conjugated to horseradish peroxidase (800 µl), diluted as recommended by the supplier, Sigma Chemical Company, St. Louis, Mo. in incubation buffer. The tubes were incubated for one hour at room temperature on a shaker following the addition of the second antibody conjugated to horseradish peroxidase. The tubes were then washed three times with 0.9% sodium chloride solution containing 0.05% Tween-20, and washed twice with borax buffer. The chemiluminescent signal was measured in a Berthold luminometer and reported in RLU units.

The results are shown in Table 11. The mean value of the antibody concentration in plasma of cancer patients, as indicated by RLU, is four times greater in cancer patients than in healthy donors. However, in a few of the healthy subjects, the antibody level as indicated by the RLU was within the range observed in the plasma of cancer patients. The maximum concentration of antibody in plasma in cancer patients was also approximately four times greater than that seen in any normal donor.

TABLE 11

NATURALLY OCCURRING ANTI-SCM ANTIBODIES IN BLOOD PLASMA

| Diagnosis | Cancer Patients Antibody Level, RLU | Age/Sex | Normal Donors Antibody Level, RLU |
|---|---|---|---|
| Ca-prostate | 80,074 | 34/M | 8,201 |
| Ca-uterus* | 29,025 | 37/M | 42,368 |
| SCC[a]-skin | 58,992 | 42/M | 91,878 |
| Ca-kidney | 75,378 | 28/M | 18,113 |
| Ca-pancreas | 59,527 | 31/M | 9,304 |
| Ca-liver | 83,523 | 50/M | 8,065 |
| Ca-ovary | 43,387 | 26/M | 13,705 |
| Ca-breast* | 71,305 | 30/M | 18,140 |
| Ca-breast | 110,840 | 38/M | 33,106 |
| Ca-breast | 88,323 | 29/M | 11,248 |
| Ca-breast | 67,381 | 36/F | 11,538 |
| Ca-lung | 90,636 | 31/M | 10,808 |
| Ca-breast* | 358,751 | 28/M | 20,217 |
| Ca-lung | 53,752 | 28/M | 6,725 |
| Mean = | 88,350 | Mean = | 21,673 |

[a]Squamous cell carcinoma
*indicates metastatic cancer

Example 21

Inhibition of SCM Factor Synthesis

Treatment of human cultured cancer cells with cycloheximide, an inhibitor of protein synthesis, decreases the amount of SCM factor produced by these cells. Similarly, ascorbic acid was shown to inhibit the synthesis of SCM factor by MCF7 human breast cancer cells in culture. The amounts of SCM factor per $7 \times 10^6$ cells in the presence or absence of $10^{-3}$ molar ascorbic acid after a 16-hour incubation were measured by the noncompetitive ELISA procedure. The results are shown in Table 12. The aliquot of cancer cells incubated in the presence of ascorbate ions produced 43.9% less SCM factor than untreated control cells. The observed inhibition of SCM factor synthesis by ascorbic acid could be the result of decreased metabolic activity of treated cancer cells since ascorbic acid was shown to selectively induce in cancer cells the transition of mitochondria into the idling, orthodox conformation, as described in L. Cercek & B. Cercek, "Effects of Ascorbate Ions on Intracellular Fluorescein Emission Polarization Spectra in Cancer and Normal Proliferating Cells," *Cancer Detection & Prevention* 10:1–20 (1987).

TABLE 12

EFFECT OF ASCORBATE IONS ON SCM FACTOR SYNTHESIS IN CULTURED MCF7 HUMAN BREAST CANCER CELLS

| Treatment During 16 hrs of Incubation at 37° C. | Corrected ELISA $A_{405}$[a] | Corrected ELISA $A_{405}$ as % of Control |
|---|---|---|
| None (Control) | 1.7448 | 100.0 |
| $1 \times 10^{-3}$M L-ascorbic acid, pH 7.1 | 0.9788 | 56.1 |

[a]Corrected ELISA $A_{405}$ = (ELISA $A_{405}$) − (Background $A_{405}$)

ADVANTAGES OF THE INVENTION

The present invention provides a means of improving therapy for cancer by potentiating the effect of lymphokines and stimulating immune defense. The stimulation of immune defense activity of lymphocytes can improve the reliability and efficacy of cancer therapy and permit the use of smaller doses of lymphokines. The ability to use smaller doses of lymphokines leads to greater toleration of these potent biological agents by the patients and the occurrence of fewer side effects.

The use of blocking agents for SCM factor-peptides can be integrated into any therapeutic regime, including chemotherapy, radiation, or surgery. The blocking agents are simple to administer and do not require additional monitoring of the patient.

Although the present invention has been described in considerable detail with regard to certain preferred versions thereof, other versions are possible. Therefore, the spirit and scope of the appended claims should not be limited to the descriptions of the preferred versions contained herein.

We claim:

1. A method for blocking suppression of at least one cell-mediated cytotoxicity mechanism selected from the group consisting of the cytotoxicity mechanisms mediated by the natural killer (NK) cells and lymphokine activated killer (LAK) cells in a cancer patient comprising administering to a cancer patient an antibody capable of blocking the activity of a peptide that suppresses a cell-mediated cytotoxicity mechanism selected from the group consisting of the cytotoxicity mechanisms mediated by the NK and LAK cells, the peptide capable of inducing a detectable decrease in the structuredness of the cytoplasmic matrix (SCM) in lymphocytes isolated from a patient with cancer (an SCM factor peptide) in a quantity sufficient to block suppression of at least one of the cytotoxicity mechanisms mediated by the NK and LAK cells to a degree such that at least one of the NK and LAK activities is about 100% as efficient as in cells in which the SCM-factor peptide is not present, as measured by lysis of susceptible target cells by lymphocytes isolated from the patient, the antibody being an antibody that specifically binds a domain of the SCM-factor peptide to inhibit the effect of the SCM-factor peptide and suppressing at least one of the cytotoxicity mechanisms mediated by NK and LAK cells, the domain being selected from the group consisting of F-L-M-I-D-Q-N-T-K-V-P-L-F-M-G-K (SEQ ID NO:2), and a domain related to (SEQ ID NO: 2) by one or more conservative amino acid substitutions selected from the group consisting of one of isoleucine, valine, and leucine for any other of isoleucine, valine, and leucine; aspartic acid for glutamic acid and vice versa; asparagine for glutamine and vice versa; and serine for threonine and vice versa.

2. The method of claim 1 wherein the antibody is autologous for the patient.

3. The method of claim 2 wherein the antibody is produced by the culture in vitro of autologous B lymphocytes producing antibodies capable of blocking the immune defense suppressive activities of the SCM-factor peptide.

4. The method of claim 1 wherein the antibody is administered in a quantity sufficient to bind substantially all of the SCM-factor peptide present in the blood plasma.

5. The method of claim 1 wherein the antibody is a monoclonal antibody.

6. The method of claim 1 wherein the domain has the sequence F-$X_{15}$-M-$X_{17}$-$X_{18}$-$X_{19}$-$X_{20}$-$X_{21}$-K-$X_{23}$-P-$X_{25}$-F-M-G-K, wherein $X_{15}$, $X_{17}$, $X_{23}$, and $X_{25}$ are each independently selected from the group consisting of I, L, and V; $X_{18}$ is selected from the group consisting of D and E; $X_{19}$ and $X_{20}$ are each independently selected from the group consisting of Q and N; and $X_{21}$ is selected from the group consisting of S and T.

7. The method of claim 6 wherein the domain has the sequence F-L-M-I-D-Q-N-T-K-V-P-L-F-M-G-K (SEQ ID NO: 2).

8. The method of claim 1 wherein the antibody is produced by immunization of an antibody-producing animal with the peptide F-L-M-I-D-Q-N-T-K-V-P-L-F-M-G-K-C (SEQ ID NO: 3) conjugated at its carboxy-terminal cysteine residue to a carrier protein.

9. The method of claim 1 wherein the antibody ms produced by immunization of an antibody-producing animal with the peptide F-N-K-P-F-V-F-L-M-I-D-Q-N-T-K-V-P-L-F-M-G-K-C (SEQ ID NO: 4) conjugated at its carboxy-terminal cysteine residue to a carrier protein.

10. The method of claim 1 wherein the blockage of suppression of the at least one cell-mediated cytotoxicity mechanism comprises a stimulation of synthesis and/or release of at least one humoral factor selected from the group consisting of interleukin-2 (IL-2) and tumor necrosis factor α (TNFα).

11. The method of claim 10 further comprising the step of determining the degree of blockage of suppression of the at least one cell-mediated cytotoxicity mechanism by monitoring an increase in synthesis and/or release of the at least one humoral factor.

12. The method of claim 1 further comprising the step of administering at least one humoral factor capable of stimulating at least one of the immune defense mechanisms mediated by the NK and LAK cells to the patient.

13. The method of claim 12 wherein the at least one humoral factor is selected from the group consisting of IL-2 and TNFα.

14. The method of claim 1 further comprising the step of administering at least one agent inhibiting the synthesis of SCM-factor peptides in tumor cells, the agent being selected from the group consisting of agents directly suppressing protein synthesis and ascorbic acid.

15. The method of claim 14 wherein the agent is an agent directly suppressing protein synthesis and the agent is selected from the group consisting of cycloheximide and actinomycin D.

16. The method of claim 14 wherein the agent is ascorbic acid.

17. A pharmaceutical composition comprising:

(a) an antibody capable of blocking the suppressive effects on at least one cell-mediated cytotoxicity mechanism selected from the group consisting of the cytotoxicity mechanisms mediated by the natural killer (NK) and the lymphokine activated killer (LAK) cells of a peptide capable of inducing a detectable decrease in the structuredness of the cytoplasmic matrix (SCM) in lymphocytes isolated from patients with cancer (an SCM-factor peptide) in a quantity sufficient to block suppression of at least one of the cell-mediated cytotoxicity mechanisms mediated by the NK and LAK cells to a degree such that at least one of the activities mediated by the NK and LAK cells is about 100% as efficient as in cells in which the SCM peptide is not present as measured by lysis of susceptible target cells by lymphocytes isolated from the patient, the antibody being an antibody that specifically binds a domain of the SCM-factor peptide to inhibit the effect of the SCM-factor peptide in suppressing at least one of the cell-mediated cytotoxicity mechanisms mediated by the NK and LAK cells, the domain being selected from the group consisting of F-L-M-I-D-Q-N-T-K-V-P-L-F-M-K (SEQ ID NO:2), and a domain related to (SEQ ID NO:2) by one or more conservative amino acid substitutions selected from the group consisting of one of isoleucine, valine, and leucine for any other of isoleucine, valine, and leucine; aspartic acid for glutamic acid and vice versa; asparagine for glutamine and vice versa; and serine for threonine and vice versa; and (b) a pharmaceutically acceptable carrier.

18. The pharmaceutical composition of claim 17 wherein the antibody is a monoclonal antibody.

19. The pharmaceutical composition of claim 17 wherein the domain has the sequence F-$X_{15}$-M-$X_{17}$-$X_{18}$-$X_{19}$-$X_{20}X_{21}$-K-$X_{23}$-P-$X_{25}$-F-M-G-K, wherein $X_{15}$, $X_{17}$, $X_{23}$, and $X_{25}$ are each independently selected from the group consisting of I, L, and V; $X_{18}$ is selected from the group consisting of D and E; $X_{19}$ and $X_{20}$ are each independently selected from the group consisting of Q and N; and $X_{21}$ is selected from the group consisting of S and T.

20. The pharmaceutical composition of claim 19 wherein the domain has the sequence F-L-M-I-D-Q-N-T-K-V-P-L-F-M-G-K (SEQ ID NO: 2).

21. The pharmaceutical composition of claim 17 wherein the antibody is produced by immunization of an antibody-producing animal with the peptide F-L-M-I-D-Q-N-T-K-V-P-L-F-M-G-K-C (SEQ ID NO: 3) conjugated at its carboxy-terminal cysteine residue to a carrier protein.

22. A kit for stimulating the immune response of a cancer patient comprising, in separate containers:

(a) the pharmaceutical composition of claim 17; and (b) a composition comprising:

(i) a lymphokine capable of stimulating at least one cell mediated cytotoxicity mechanism selected from the group consisting of the cytotoxicity mechanisms mediated by the natural killer (NK) and lymphokine activated killer (LAK) cells in a quantity sufficient to stimulate cytotoxicity; and (ii) a pharmaceutically acceptable carrier.

23. The kit of claim 22 wherein the lymphokine is selected from the group consisting of interleukin-2, tumor necrosis factor α and interferon.

24. The kit of claim 23 wherein the lymphokine is interleukin-2.

25. The kit of claim 23 wherein the lymphokine is tumor necrosis factor α.

26. The kit of claim 22 further comprising, in a separate container:

(c) an inhibitor of protein synthesis with specific effects on tumor cells, optionally with a pharmaceutically acceptable carrier.

27. The kit of claim 26 wherein the inhibitor of protein synthesis is selected from the group consisting of actinomycin D and cycloheximide.

28. The kit of claim 26 wherein the inhibitor of protein synthesis is ascorbic acid.

29. The method of claim 1 wherein the domain is a domain related to the domain F-L-M-I-D-Q-N-T-K-V-P-L-F-M-G-K (SEQ ID NO: 2) by one or more conservative amino acid substitutions selected from the group consisting of one of isoleucine, valine, and leucine for any other of isoleucine, valine, and leucine; aspartic acid for glutamic acid and vice versa; asparagine for glutamine and vice versa; and serine for threonine and vice versa, the domain including therein a core sequence of nine amino acid residues having an amphipathicity profile substantially equivalent to that of the sequence F-L-M-I-D-Q-N-T-K (SEQ ID NO: 5), wherein the sixth amino acid of the core sequence is selected from the group consisting of Q and N, the seventh amino acid of the core sequence is selected from the group consisting of N and Q, and the ninth amino acid of the core sequence is selected from the group consisting of K and R.

30. The method of claim 29 wherein the domain includes therein the core sequence F-L-M-I-D-Q-N-T-K (SEQ ID NO: 5).

* * * * *

SEQUENCE LISTING ( 1 ) GENERAL INFORMATION:

( i i i ) NUMBER OF SEQUENCES: 24

( 2 ) INFORMATION FOR SEQ ID NO:1:

( i ) SEQUENCE CHARACTERISTICS:
      ( A ) LENGTH: 22 amino acids
      ( B ) TYPE: amino acid
      ( D ) TOPOLOGY: linear ( i i ) MOLECULE TYPE: peptide ( i i i ) HYPOTHETICAL: NO ( i v ) ANTI-SENSE: NO ( v i ) ORIGINAL SOURCE:
      ( A ) ORGANISM: Homo sapiens ( x i ) SEQUENCE DESCRIPTION: SEQ ID NO:1:

Phe  Asn  Lys  Pro  Phe  Val  Phe  Leu  Met  Ile  Asp  Gln  Asn  Thr  Lys  Val
   1                  5                           10                          15

Pro  Leu  Phe  Met  Gly  Lys
                  20

( 2 ) INFORMATION FOR SEQ ID NO:2:

( i ) SEQUENCE CHARACTERISTICS:
      ( A ) LENGTH: 16 amino acids
      ( B ) TYPE: amino acid
      ( D ) TOPOLOGY: linear ( i i ) MOLECULE TYPE: peptide ( i i i ) HYPOTHETICAL: NO ( i v ) ANTI-SENSE: NO ( v i ) ORIGINAL SOURCE:
      ( A ) ORGANISM: Homo sapiens ( x i ) SEQUENCE DESCRIPTION: SEQ ID NO:2:

Phe  Leu  Met  Ile  Asp  Gln  Asn  Thr  Lys  Val  Pro  Leu  Phe  Met  Gly  Lys
   1                  5                           10                          15

( 2 ) INFORMATION FOR SEQ ID NO:3:

( i ) SEQUENCE CHARACTERISTICS:
      ( A ) LENGTH: 17 amino acids
      ( B ) TYPE: amino acid
      ( D ) TOPOLOGY: linear ( i i ) MOLECULE TYPE: peptide ( i i i ) HYPOTHETICAL: NO ( i v ) ANTI-SENSE: NO ( v i ) ORIGINAL SOURCE:
      ( A ) ORGANISM: Homo sapiens ( x i ) SEQUENCE DESCRIPTION: SEQ ID NO:3:

Phe  Leu  Met  Ile  Asp  Gln  Asn  Thr  Lys  Val  Pro  Leu  Phe  Met  Gly  Lys
   1                  5                           10                          15

Cys ( 2 ) INFORMATION FOR SEQ ID NO:4:

(i) SEQUENCE CHARACTERISTICS:
 (A) LENGTH: 23 amino acids
 (B) TYPE: amino acid
 (D) TOPOLOGY: linear (ii) MOLECULE TYPE: peptide (iii) HYPOTHETICAL: NO (iv) ANTI-SENSE: NO (vi) ORIGINAL SOURCE:
 (A) ORGANISM: Homo sapiens (xi) SEQUENCE DESCRIPTION: SEQ ID NO:4:

```
Phe Asn Lys Pro Phe Val Phe Leu Met Ile Asp Gln Asn Thr Lys Val
1               5                   10                  15

Pro Leu Phe Met Gly Lys Cys
            20
```

(2) INFORMATION FOR SEQ ID NO:5:

(i) SEQUENCE CHARACTERISTICS:
 (A) LENGTH: 9 amino acids
 (B) TYPE: amino acid
 (D) TOPOLOGY: linear (ii) MOLECULE TYPE: peptide (iii) HYPOTHETICAL: NO (iv) ANTI-SENSE: NO (vi) ORIGINAL SOURCE:
 (A) ORGANISM: Homo sapiens (xi) SEQUENCE DESCRIPTION: SEQ ID NO:5:

```
Phe Leu Met Ile Asp Gln Asn Thr Lys
1               5
```

(2) INFORMATION FOR SEQ ID NO:6:

(i) SEQUENCE CHARACTERISTICS:
 (A) LENGTH: 29 amino acids
 (B) TYPE: amino acid
 (D) TOPOLOGY: linear (ii) MOLECULE TYPE: peptide (iii) HYPOTHETICAL: NO (iv) ANTI-SENSE: NO (vi) ORIGINAL SOURCE:
 (A) ORGANISM: Homo sapiens (ix) FEATURE:
 (A) NAME/KEY: Region
 (B) LOCATION: 1..23
 (D) OTHER INFORMATION: /label=mutation
  /note="Naturally-occurring variants: amino acid 1
  is S not M, amino acid 5 is D not E, or amino acid
  23 is T not V"

(xi) SEQUENCE DESCRIPTION: SEQ ID NO:6:

```
Met Ile Pro Pro Glu Val Lys Phe Asn Lys Pro Phe Val Phe Leu Met
1               5                   10                  15

Ile Asp Gln Asn Thr Lys Val Pro Leu Phe Met Gly Lys
            20                  25
```

(2) INFORMATION FOR SEQ ID NO:7:

( i ) SEQUENCE CHARACTERISTICS:
   ( A ) LENGTH: 21 amino acids
   ( B ) TYPE: amino acid
   ( D ) TOPOLOGY: linear ( i i ) MOLECULE TYPE: peptide ( i i i ) HYPOTHETICAL: NO ( i v ) ANTI-SENSE: NO ( v i ) ORIGINAL SOURCE:
   ( A ) ORGANISM: Homo sapiens ( x i ) SEQUENCE DESCRIPTION: SEQ ID NO:7:

```
Met Ile Pro Pro Glu Val Lys Phe Asn Lys Pro Phe Val Phe Leu Met
 1               5                  10                  15
Asp Gln Asn Thr Lys
             20
```

( 2 ) INFORMATION FOR SEQ ID NO:8:

( i ) SEQUENCE CHARACTERISTICS:
      ( A ) LENGTH: 15 amino acids
      ( B ) TYPE: amino acid
      ( D ) TOPOLOGY: linear ( i i ) MOLECULE TYPE: peptide ( i i i ) HYPOTHETICAL: NO ( i v ) ANTI-SENSE: NO ( v i ) ORIGINAL SOURCE:
      ( A ) ORGANISM: Homo sapiens ( x i ) SEQUENCE DESCRIPTION: SEQ ID NO:8:

```
Phe Asn Lys Pro Phe Val Phe Leu Met Ile Asp Gln Asn Thr Lys
 1               5                  10                  15
```

( 2 ) INFORMATION FOR SEQ ID NO:9:

( i ) SEQUENCE CHARACTERISTICS:
      ( A ) LENGTH: 14 amino acids
      ( B ) TYPE: amino acid
      ( D ) TOPOLOGY: linear ( i i ) MOLECULE TYPE: peptide ( i i i ) HYPOTHETICAL: NO ( i v ) ANTI-SENSE: NO ( v i ) ORIGINAL SOURCE:
      ( A ) ORGANISM: Homo sapiens ( x i ) SEQUENCE DESCRIPTION: SEQ ID NO:9:

```
Met Ile Pro Pro Glu Val Lys Phe Asn Lys Pro Phe Val Phe
 1               5                  10
```

( 2 ) INFORMATION FOR SEQ ID NO:10:

( i ) SEQUENCE CHARACTERISTICS:
      ( A ) LENGTH: 8 amino acids
      ( B ) TYPE: amino acid
      ( D ) TOPOLOGY: linear ( i i ) MOLECULE TYPE: peptide ( i i i ) HYPOTHETICAL: NO ( i v ) ANTI-SENSE: NO ( v i ) ORIGINAL SOURCE:
      ( A ) ORGANISM: Homo sapiens ( x i ) SEQUENCE DESCRIPTION: SEQ ID NO:10:

```
Phe  Trp  Gly  Ala  Glu  Gly  Gln  Arg
1                   5
```

( 2 ) INFORMATION FOR SEQ ID NO:11:

( i ) SEQUENCE CHARACTERISTICS:
          ( A ) LENGTH: 9 amino acids
          ( B ) TYPE: amino acid
          ( D ) TOPOLOGY: linear ( i i ) MOLECULE TYPE: peptide ( i i i ) HYPOTHETICAL: NO ( i v ) ANTI-SENSE: NO ( v i ) ORIGINAL SOURCE:
          ( A ) ORGANISM: Homo sapiens ( x i ) SEQUENCE DESCRIPTION: SEQ ID NO:11:

```
Phe  Ser  Trp  Gly  Ala  Glu  Gly  Gln  Arg
1                   5
```

( 2 ) INFORMATION FOR SEQ ID NO:12:

( i ) SEQUENCE CHARACTERISTICS:
          ( A ) LENGTH: 7 amino acids
          ( B ) TYPE: amino acid
          ( D ) TOPOLOGY: linear ( i i ) MOLECULE TYPE: peptide ( i i i ) HYPOTHETICAL: NO ( i v ) ANTI-SENSE: NO ( v i ) ORIGINAL SOURCE:
          ( A ) ORGANISM: Homo sapiens ( x i ) SEQUENCE DESCRIPTION: SEQ ID NO:12:

```
Met  Ile  Pro  Pro  Glu  Val  Lys
1                   5
```

( 2 ) INFORMATION FOR SEQ ID NO:13:

( i ) SEQUENCE CHARACTERISTICS:
          ( A ) LENGTH: 30 amino acids
          ( B ) TYPE: amino acid
          ( D ) TOPOLOGY: linear ( i i ) MOLECULE TYPE: peptide ( i i i ) HYPOTHETICAL: NO ( i v ) ANTI-SENSE: NO ( v i ) ORIGINAL SOURCE:
          ( A ) ORGANISM: Homo sapiens ( x i ) SEQUENCE DESCRIPTION: SEQ ID NO:13:

```
Met  Ile  Pro  Pro  Glu  Val  Lys  Phe  Asn  Lys  Pro  Phe  Val  Phe  Leu  Met
1                   5                        10                       15
Ile  Asp  Gln  Asn  Thr  Lys  Val  Pro  Leu  Phe  Met  Gly  Lys  Cys
                    20                       25                       30
```

( 2 ) INFORMATION FOR SEQ ID NO:14:

( i ) SEQUENCE CHARACTERISTICS:
  ( A ) LENGTH: 29 amino acids
  ( B ) TYPE: amino acid
  ( D ) TOPOLOGY: linear ( i i ) MOLECULE TYPE: peptide ( i i i ) HYPOTHETICAL: NO ( i v ) ANTI-SENSE: NO ( v i ) ORIGINAL SOURCE:
  ( A ) ORGANISM: Homo sapiens ( i x ) FEATURE:
  ( A ) NAME/KEY: Region
  ( B ) LOCATION: 1..23
  ( D ) OTHER INFORMATION: /label=mutation
    / note="Variant exists with M at amino acid 1
    instead of V and with V at amino acid 23 instead
    of T"

( x i ) SEQUENCE DESCRIPTION: SEQ ID NO:14:

Val Ile Pro Pro Glu Val Lys Phe Asn Lys Pro Phe Val Phe Leu Met
1               5                   10                  15

Ile Asp Gln Asn Thr Lys Thr Pro Leu Phe Met Gly Lys
            20                  25

( 2 ) INFORMATION FOR SEQ ID NO:15:

( i ) SEQUENCE CHARACTERISTICS:
  ( A ) LENGTH: 29 amino acids
  ( B ) TYPE: amino acid
  ( D ) TOPOLOGY: linear ( i i ) MOLECULE TYPE: peptide ( i i i ) HYPOTHETICAL: NO ( i v ) ANTI-SENSE: NO ( v i ) ORIGINAL SOURCE:
  ( A ) ORGANISM: Homo sapiens ( x i ) SEQUENCE DESCRIPTION: SEQ ID NO:15:

Met Ile Pro Pro Glu Val Lys Phe Asn Lys Pro Phe Val Phe Leu Met
1               5                   10                  15

Ile Asp Gln Asn Thr Lys Cys Pro Cys Phe Met Gly Cys
            20                  25

( 2 ) INFORMATION FOR SEQ ID NO:16:

( i ) SEQUENCE CHARACTERISTICS:
  ( A ) LENGTH: 29 amino acids
  ( B ) TYPE: amino acid
  ( D ) TOPOLOGY: linear ( i i ) MOLECULE TYPE: peptide ( i i i ) HYPOTHETICAL: NO ( i v ) ANTI-SENSE: NO ( v i ) ORIGINAL SOURCE:
  ( A ) ORGANISM: Homo sapiens ( i x ) FEATURE:
  ( A ) NAME/KEY: Region
  ( B ) LOCATION: 1..2
  ( D ) OTHER INFORMATION: /label=mutation
    / note="Variant exists in which amino acid 1 is V
    instead of M"

( x i ) SEQUENCE DESCRIPTION: SEQ ID NO:16:

Met Ile Pro Pro Glu Val Lys Phe Asn Lys Pro Phe Val Phe Leu Met
1               5                   10                  15

Ile Asp Gln Asn Thr Lys Cys Cys Leu Phe Met Gly Lys
            20                  25

( 2 ) INFORMATION FOR SEQ ID NO:17:

( i ) SEQUENCE CHARACTERISTICS:
        ( A ) LENGTH: 29 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v i ) ORIGINAL SOURCE:
        ( A ) ORGANISM: Homo sapiens ( i x ) FEATURE:
        ( A ) NAME/KEY: Region
        ( B ) LOCATION: 1..2
        ( D ) OTHER INFORMATION: /label=mutation
         / note="Variant exists in which amino acid 1 is S
         instead of R"

( x i ) SEQUENCE DESCRIPTION: SEQ ID NO:17:

Arg Ile Pro Pro Glu Val Lys Phe Asn Lys Pro Phe Val Phe Leu Met
1               5                   10                  15

Ile Asp Gln Asn Thr Lys Arg Pro Leu Phe Met Gly Lys
            20                  25

( 2 ) INFORMATION FOR SEQ ID NO:18:

( i ) SEQUENCE CHARACTERISTICS:
        ( A ) LENGTH: 29 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:18:

Val Ile Pro Pro Glu Val Lys Phe Asn Lys Pro Phe Val Phe Leu Met
1               5                   10                  15

Ile Asp Gln Asn Thr Lys Cys Pro Leu Phe Met Gly Lys
            20                  25

( 2 ) INFORMATION FOR SEQ ID NO:19:

( i ) SEQUENCE CHARACTERISTICS:
        ( A ) LENGTH: 29 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v i ) ORIGINAL SOURCE:

(A) ORGANISM: Homo sapiens (x i) SEQUENCE DESCRIPTION: SEQ ID NO:19:

```
Val Ile Pro Pro Glu Val Lys Phe Asn Cys Pro Phe Val Phe Leu Met
1               5                   10                  15

Ile Asp Gln Asn Thr Lys Val Pro Leu Phe Met Gly Lys
                20                  25
```

(2) INFORMATION FOR SEQ ID NO:20:

(i) SEQUENCE CHARACTERISTICS:
        (A) LENGTH: 29 amino acids
        (B) TYPE: amino acid
        (D) TOPOLOGY: linear (ii) MOLECULE TYPE: peptide (iii) HYPOTHETICAL: NO (iv) ANTI-SENSE: NO (vi) ORIGINAL SOURCE:
        (A) ORGANISM: Homo sapiens (ix) FEATURE:
        (A) NAME/KEY: Region
        (B) LOCATION: 1..2
        (D) OTHER INFORMATION: /label=mutation
            / note="Variant exists in which amino acid 1 is S
            instead of R"

(x i) SEQUENCE DESCRIPTION: SEQ ID NO:20:

```
Arg Ile Pro Pro Glu Val Lys Phe Asn Lys Pro Phe Val Phe Leu Met
1               5                   10                  15

Ile Asp Gln Asn Thr Lys Cys Pro Cys Phe Met Gly Cys
                20                  25
```

(2) INFORMATION FOR SEQ ID NO:21:

(i) SEQUENCE CHARACTERISTICS:
        (A) LENGTH: 35 amino acids
        (B) TYPE: amino acid
        (D) TOPOLOGY: linear (ii) MOLECULE TYPE: peptide (iii) HYPOTHETICAL: NO (iv) ANTI-SENSE: NO (vi) ORIGINAL SOURCE:
        (A) ORGANISM: Homo sapiens (x i) SEQUENCE DESCRIPTION: SEQ ID NO:21:

```
Arg Ile Pro Pro Glu Val Lys Phe Asn Lys Pro Phe Val Phe Leu Met
1               5                   10                  15

Ile Asp Gln Asn Thr Lys Cys Pro Cys Phe Met Gly Cys Val Val Asn
                20                  25                  30

Cys Thr Glu
        35
```

(2) INFORMATION FOR SEQ ID NO:22:

(i) SEQUENCE CHARACTERISTICS:
        (A) LENGTH: 29 amino acids
        (B) TYPE: amino acid
        (D) TOPOLOGY: linear (ii) MOLECULE TYPE: peptide 5,580,561

57 58

-continued ( i i i ) HYPOTHETICAL: NO ( i v ) ANTI-SENSE: NO ( v i ) ORIGINAL SOURCE:
      ( A ) ORGANISM: Homo sapiens ( i x ) FEATURE:
      ( A ) NAME/KEY: Region
      ( B ) LOCATION: 1..2
      ( D ) OTHER INFORMATION: /label=mutation
          / note="Variant exists in which amino acid 1 is S
          instead of V"

( x i ) SEQUENCE DESCRIPTION: SEQ ID NO:22:

```
Val Ile Pro Pro Glu Val Lys Phe Asn Lys Pro Phe Val Phe Leu Met
1               5                   10                  15

Ile Glu Gln Asn Thr Lys Ser Pro Leu Phe Met Gly Lys
                20                  25
```

( 2 ) INFORMATION FOR SEQ ID NO:23:

( i ) SEQUENCE CHARACTERISTICS:
      ( A ) LENGTH: 35 amino acids
      ( B ) TYPE: amino acid
      ( D ) TOPOLOGY: linear ( i i ) MOLECULE TYPE: peptide ( i i i ) HYPOTHETICAL: NO ( i v ) ANTI-SENSE: NO ( v i ) ORIGINAL SOURCE:
      ( A ) ORGANISM: Homo sapiens ( x i ) SEQUENCE DESCRIPTION: SEQ ID NO:23:

```
Val Ile Pro Pro Glu Val Lys Phe Asn Lys Pro Phe Val Phe Leu Met
1               5                   10                  15

Ile Glu Gln Asn Thr Lys Ser Pro Leu Phe Met Gly Lys Val Val Asn
                20                  25                  30

Pro Thr Gln
            35
```

( 2 ) INFORMATION FOR SEQ ID NO:24:

( i ) SEQUENCE CHARACTERISTICS:
      ( A ) LENGTH: 35 amino acids
      ( B ) TYPE: amino acid
      ( D ) TOPOLOGY: linear ( i i ) MOLECULE TYPE: peptide ( i i i ) HYPOTHETICAL: NO ( i v ) ANTI-SENSE: NO ( v i ) ORIGINAL SOURCE:
      ( A ) ORGANISM: Homo sapiens ( i x ) FEATURE:
      ( A ) NAME/KEY: Region
      ( B ) LOCATION: 1..2
      ( D ) OTHER INFORMATION: /label=mutation
          / note="Variant exists in which amino acid 1 is V
          instead of S"

( x i ) SEQUENCE DESCRIPTION: SEQ ID NO:24:

```
Ser Ile Pro Pro Glu Val Lys Phe Asn Lys Pro Phe Val Phe Leu Met
1               5                   10                  15

Ile Glu Gln Asn Thr Lys Ser Pro Leu Phe Met Gly Lys Val Val Asn
```

```
                    20                    25                    30
Pro Thr Gln
         35
```